US012102678B2

(12) United States Patent
Kok et al.

(10) Patent No.: US 12,102,678 B2
(45) Date of Patent: Oct. 1, 2024

(54) VACCINE BOOSTER COMPOSITIONS FOR RESPIRATORY VIRAL DISEASES

(71) Applicant: Centre for Virology, Vaccinology and Therapeutics Limited, Hong Kong (CN)

(72) Inventors: Kin Hang Kok, Hong Kong (CN); Kwok Yung Yuen, Hong Kong (CN); Joy Yan Lam, Hong Kong (CN)

(73) Assignee: Centre for Virology, Vaccinology and Therapeutics Limited, Hong Kong (CN)

( * ) Notice: Subject to any disclaimer, the term of this patent is extended or adjusted under 35 U.S.C. 154(b) by 0 days.

(21) Appl. No.: 18/452,741

(22) Filed: Aug. 21, 2023

(65) Prior Publication Data

US 2024/0024461 A1 Jan. 25, 2024

Related U.S. Application Data

(63) Continuation of application No. PCT/CN2022/106843, filed on Jul. 20, 2022.

(60) Provisional application No. 63/319,214, filed on Mar. 11, 2022.

(51) Int. Cl.

| | |
|---|---|
| ***A61K 39/215*** | (2006.01) |
| ***A61K 9/00*** | (2006.01) |
| ***A61P 31/14*** | (2006.01) |
| ***C07K 14/165*** | (2006.01) |
| *A61K 39/00* | (2006.01) |

(52) U.S. Cl.

CPC .......... *A61K 39/215* (2013.01); *A61K 9/0043* (2013.01); *A61P 31/14* (2018.01); *C07K 14/165* (2013.01); *A61K 2039/543* (2013.01); *A61K 2039/545* (2013.01)

(58) Field of Classification Search

CPC ... A61P 31/14; C07K 14/165; C07K 2319/00; C07K 2319/70; G01N 2333/165; C12N 2770/20071; C12N 2770/20034; C12N 2770/20022; A61K 2039/53; A61K 39/215; C07D 401/06

See application file for complete search history.

(56) References Cited

U.S. PATENT DOCUMENTS

| | | | | |
|---|---|---|---|---|
| 11,382,968 | B2 * | 7/2022 | Georges | C07K 14/005 |
| 2021/0379181 | A1 | 12/2021 | Rauch et al. | |
| 2022/0016234 | A1 | 1/2022 | Rice et al. | |
| 2024/0024461 | A1 | 1/2024 | Kok | |
| 2024/0139307 | A1 | 5/2024 | Kok | |

FOREIGN PATENT DOCUMENTS

| | | | |
|---|---|---|---|
| CN | 111939250 A | 11/2020 | |
| WO | 2021156267 A1 | 8/2021 | |
| WO | 2021159040 A2 | 8/2021 | |
| WO | 2023168880 A1 | 9/2023 | |

OTHER PUBLICATIONS

Rice et al. bioRxiv posted Jul. 30, 2020, pp. 1-36.*
Zsofia Hevesi et al. bioRxiv posted Feb. 15, 2022, pp. 1-19.*
Cheng et al. bioRxiv preprint doi: posted on Aug. 20, 2020, pp. 1-24.*
Castro et al. bioRxivv , posted on Sep. 16, 2021 , pp. 1-24.*
International Search Report and Written Opinion mailed on Dec. 15, 2022, for PCT Application No. PCT/CN2022/106843, filed on Jul. 20, 2022, 11 pages.
U.S. Appl. No. 18/165,286, filed Feb. 6, 2023 for Kin Hang Kok et al. (U.S. Patent Application is not submitted herewith pursuant to the waiver of 37 C.F.R. §1.98(a)(2)(iii) issued by the Office on Sep. 21, 2004.).
Hoffmann, M. et al. (Apr. 16, 2020). "SARS-CoV-2 Cell Entry Depends on ACE2 and TMPRSS2 and Is Blocked by a Clinically Proven Protease Inhibitor," Cell 181(2):271-280.
Lam, J. Y. et al. (2022). "A Nasal Omicron Vaccine Booster Elicits Potent Neutralizing Antibody Response Against Emerging SARS-CoV-2 Variants," Emerging Microbes and Infections 11(1):964-967.
Li, F. et al. (Sep. 16, 2005). "Structure of SARS Coronavirus Spike Receptor-Binding Domain Complexed with Receptor," Science 309(5742):1864-1868.
Lu, G. et al. (Aug. 8, 2013, e-pub Jul. 7, 2013). "Molecular Basis of Binding Between Novel Human Coronavirus MERS-CoV and its Receptor CD26," Nature 500:227-231.
Millet, J. K. et al. (Apr. 16, 2015, e-pub Nov. 22, 2014). "Host Cell Proteases: Critical Determinants of Coronavirus Tropism and Pathogenesis," Virus Res. 202:120-134.
Scheraga, H. A. (1992). "Predicting Three-Dimensional Structures of Oligopeptides," Rev. Computational Chem. 3:73-142.
Walls, A. C. et al. (Apr. 16, 2020). "Structure, Function, and Antigenicity of the SARS-CoV-2 Spike Glycoprotein," Cell 180(2):281-292.
Wang, Q. et al. (May 14, 2020). "Structural and Functional Basis of SARS-CoV-2 Entry by Using Human ACE2," Cell 181(4):894-904.
Zhou, P. et al. (Mar. 12, 2020, e-pub. Feb. 3, 2020). "A Pneumonia Outbreak Associated With a New 9 Coronavirus of Probable Bat Origin," Nature 579:270-273, 20 pages.
U.S. Appl. No. 18/452,741, filed Aug. 21, 2023, for Kin Hang Kok et al. (U.S. Patent Application is not submitted herewith pursuant to the waiver of 37 C.F.R. §1.98(a)(2)(iii) issued by the Office on Sep. 21, 2004.).

* cited by examiner

*Primary Examiner* — Bao Q Li
(74) *Attorney, Agent, or Firm* — Morrison & Foerster LLP

(57) ABSTRACT

The present application provides chimeric proteins comprising comprising a receptor binding domain ("RBD") of a SARS-CoV-2 spike protein ("S protein") fused to a booster enhancer domain ("BED") and uses thereof as vaccine or vaccine booster compositions. Also provided are method of boostering SARS-CoV-2 vaccines by administering to a vaccinated individual an effective amount of the vaccine booster composition, wherein the vaccine booster composition comprises a spike protein or a fragment thereof, and optionally wherein the vaccine booster composition is administered intranasally.

25 Claims, 7 Drawing Sheets

Specification includes a Sequence Listing.

authentic SARS-CoV-2 neutralization authentic SARS-CoV-2 neutralization

VACCINE BOOSTER COMPOSITIONS FOR RESPIRATORY VIRAL DISEASES

CROSS REFERENCE TO RELATED APPLICATIONS

This application is a continuation of International Application No. PCT/CN2022/106843, filed Jul. 20, 2022, which claims the priority benefit of U.S. Provisional Application No. 63/319,214, filed Mar. 11, 2022, the contents of each of which are incorporated herein by reference in their entirety.

REFERENCE TO AN ELECTRONIC SEQUENCE LISTING

The contents of the electronic sequence listing (253322000101SEQLIST.xml; Size: 9,332 bytes; and Date of Creation: Jan. 11, 2023) is herein incorporated by reference in its entirety.

FIELD OF THE INVENTION

The invention relates to compositions and methods for preventing or treating respiratory viral infections, such as coronavirus infections.

BACKGROUND

As of Jan. 26, 2022, the SARS-CoV-2 virus has accounted for more than 350 million confirmed cases of infection worldwide. Vaccination remains the most effective preventive measure against the disease. Currently, three types of COVID-19 vaccines have been widely employed, including inactivated whole virions, adenovirus and mRNA vaccines. Two doses of intramuscular vaccination of either of the vaccines generally elicits high-level neutralizing antibodies (nAbs) that can effectively neutralize the original SARS-CoV-2 and the subsequently emerged variant strains (for examples alpha and beta variants), but to a lesser extent to delta variants. However, the recently emerged omicron variant encodes a spike protein carrying more than 30 mutations, some of which are located at the binding sites of neutralizing antibodies. As a result, people previously vaccinated with two doses of vaccine have markedly reduced nAbs level against the circulating omicron variant. In view of the compromised neutralization against the most recently emerged omicron variant, plus the significant decline of nAb level after 4-6 months of vaccination, a third dose of vaccination has been suggested and is already implemented in some countries.

BRIEF SUMMARY

The present application provides methods of enhancing the effect of a vaccine against SARS-CoV-2 in an individual who has been vaccinated, comprising administering to the individual an effective amount of a vaccine booster composition. Also provided are chimeric proteins, including a chimeric protein comprising a receptor binding domain ("RBD") of a SARS-CoV-2 spike protein ("S protein") fused to a booster enhancer domain ("BED"). The present application further provides vaccine booster compositions comprising the chimeric protein, as well as methods of enhancing the effect of a vaccine against SARS-CoV-2 in an individual who has been vaccinated by use of the vaccine booster compositions.

One aspect of the present application provides methods of enhancing the effect of a vaccine against SARS-CoV-2 in an individual who has been vaccinated, comprising administering to the individual an effective amount of a vaccine booster composition, wherein the vaccine booster composition comprises a spike protein or a fragment thereof. In some embodiments, the vaccine booster composition is administered intranasally. In some embodiments, the vaccine booster composition is administered at least 7 days after the administration of the vaccine. In some embodiments, the vaccine booster composition is administered after about 4 to about 6 weeks after the administration of the vaccine. In some embodiments, the individual has been administered with at least two doses of the vaccine prior to the administration of the vaccine booster composition. In some embodiments, the vaccine is administered intramuscularly, intranasally, or intradermally. In some embodiments, the vaccine is an mRNA-based vaccine, a recombinant virus-based vaccine, an inactivated virus-based vaccine, a subunit vaccine or a combination thereof. In some embodiments, the individual is a human. In some embodiments, the vaccine booster composition further comprises an adjuvant selected from the group consisting of a nucleic acid, a cytokine, or alum. In some embodiments, the vaccine booster composition does not comprise an adjuvant.

One aspect of the present application provides chimeric proteins, wherein the chimeric protein comprises a receptor binding domain ("RBD") of a SARS-CoV-2 spike protein ("S protein") fused to a booster enhancer domain ("BED"). In some embodiments, the RBD is derived from an S protein of SARS-CoV-2 lineage A (SEQ ID NO:1). In some embodiments, the RBD is derived from an S protein of the omicron variant of SARS-CoV-2 (SARS-CoV-2 lineage B.1.1.529) (SEQ ID NO:2). In some embodiments, the RBD comprises amino acids 306-541 of SEQ ID NO:1 or amino acids 303-538 of SEQ ID NO:2. In some embodiments, the RBD is about 200 to about 300 amino acids long. In some embodiments, the BED is derived from a protein of a coronavirus. In some embodiments, the BED is derived from a protein of a SARS-CoV-2 virus. In some embodiments, the BED is derived from the N protein of a SARS-CoV-2 virus. In some embodiments, the BED is derived from the N protein of SARS-CoV-2 (SEQ ID NO:3). In some embodiments, the BED comprises amino acids 44-180 of SEQ ID NO:3. In some embodiments, the BED is about 100 to about 150 amino acids long. In some embodiments, the BED is fused directly to the RBD. In some embodiments, the BED is fused to the RBD via a linker. In some embodiments, the BED is fused to the C-terminus of the RBD. In some embodiments, the BED is fused to the N-terminus of the RBD. Also provided are nucleic acids encoding any one of the chimeric protein described herein, as well as vectors comprising any of the nucleic acids described herein. In some embodiments, provided are methods of producing any one of the chimeric proteins described herein, the method comprising expressing the nucleic acid in a host cell, thereby obtaining the chimeric protein. In some embodiments, the host cell is a mammalian cell.

One aspect of the present application provides vaccine booster compositions, wherein the vaccine booster composition comprises any one of the chimeric proteins described herein. In some embodiments, the vaccine booster composition further comprises an adjuvant selected from the group consisting of a nucleic acid, a cytokine, or alum. In some embodiments, the vaccine booster composition does not comprise an adjuvant.

Another aspect of the present application provides methods of enhancing the effect of a vaccine against SARS-CoV-2 in an individual who has been vaccinated, the method comprising administering to the individual an effective amount of any one of the vaccine booster compositions described herein. In some embodiments, the vaccine booster composition is administered intranasally. In some embodiments, the vaccine booster composition is administered at least 7 days after the administration of the vaccine. In some embodiments, the vaccine booster composition is administered after about 4 to about 6 weeks after the administration of the vaccine. In some embodiments, the individual has been administered with at least two doses of the vaccine prior to the administration of the vaccine booster composition. In some embodiments, the vaccine is administered intramuscularly, intranasally, or intradermally. In some embodiments, the vaccine is an mRNA-based vaccine, a recombinant virus-based vaccine, an inactivated virus-based vaccine, a subunit vaccine, or a combination thereof. In some embodiments, the individual is a human.

Also provided are kits and articles of manufacture comprising any one of the compositions described above and instructions for any one of the methods described above.

BRIEF DESCRIPTION OF THE DRAWINGS

The drawings illustrate certain embodiments of the features and advantages of this disclosure. These embodiments are not intended to limit the scope of the appended claims in any manner

DETAILED DESCRIPTION

Figure 1A:
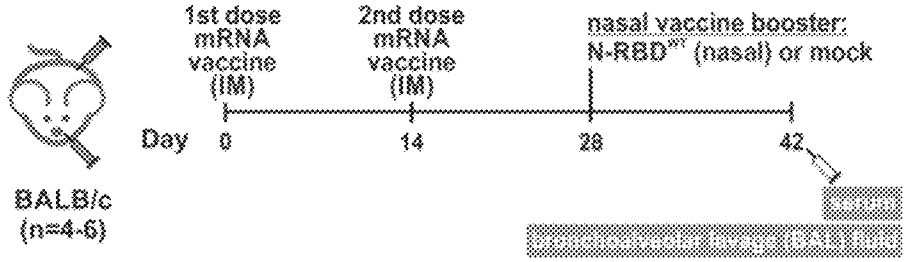
FIG. 1A shows the schematics of the experimental design for a nasal vaccine booster. All mice were intramuscularly injected with 2 doses of COVID-19 mRNA vaccine (1 μg per mouse), at 14 days apart. At day 28, 18 μg N-RBD$^{WT}$ (recombinant SARS-CoV-2 spike RBD fused with nucleocapsid NTD) was administered intranasally for the booster group (n=4 biological replicates). PBS was given intranasally for the control group (n=6 biological replicates). Sera and bronchoalveolar lavage (BAL) fluids were collected at day 42.

The present application provides methods and compositions for boosting antibody response of SARS-CoV-2 vaccines, which is believed to be required to maintain the level of neutralizing antibodies (nAbs) high enough to combat the future emerging variants. Specifically, the inventors have designed and tested the novel idea of using recombinant protein as nasal vaccine booster to boost the nAbs level against SARS-CoV-2, and demonstrated the superior efficacy of intrasanally administered vaccine booster compositions (e.g., N-RBD$^{WT}$ and N-RBD$^{omicron}$) in boosting SARS-CoV-2-specific antibody response. The high neutralizing titer against omicron variant also suggested the ability of the protein booster to prevent omicron viral infection. Without being bound by theory, it is believed that use of recombinant protein as vaccine has a number of advantages: 1) The production is cost-effective as high yield production of recombinant protein could be easily achieved; 2) The recombinant protein vaccine is stable at room temperature or 4° C. and so cold chain at very low temperature (−20° C. or −80° C.) is not required; 3) Nasal spray of protein vaccine is comparably less invasive than intramuscular injection and could potentially improve induction of mucosal immunity to combat infections of the mucosa; and 4) Nasal spray of recombinant protein vaccine does not involve handling of infectious materials and thus does not involve the safety concerns associated with infectious materials.

Accordingly, the present application in one aspect provides a method of enhancing the effect of a vaccine against SARS-CoV-2 in an individual who has been vaccinated, comprising administering (e.g., intranasally administering) to the individual an effective amount of the vaccine booster composition, wherein the vaccine booster composition comprises a spike protein (such as a recombinant protein comprising a receptor binding domain ("RBD") of a SARS-CoV-2 spike protein ("S protein")) or a fragment thereof, optionally fused to a booster enhancer domain ("BED").

In another aspect, there is provided a chimeric protein comprising a receptor binding domain ("RBD") of a SARS-CoV-2 spike protein ("S protein") fused to a booster enhancer domain ("BED"). In some embodiments, the BED is derived from a nucleocapsid protein of a coronavirus (such as a SARS-CoV-2 virus).

Also provided are nucleic acids encoding the chimeric proteins described herein and methods of using the chimeric proteins as SARS-CoV-2 vaccine or vaccine boosters.

I. Definitions

As used herein, "treatment" or "treating" is an approach for obtaining beneficial or desired results including clinical results. For purposes of this application, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of the disease. The methods of the present application contemplate any one or more of these aspects of treatment.

"Preventing," as used herein, includes providing prophylaxis with respect to the occurrence or recurrence of a disease in a subject that may be predisposed to the disease but has not yet been diagnosed with the disease.

The terms "individual," "subject" and "patient" are used interchangeably herein to describe a mammal, including humans. In some embodiments, the individual is human. In some embodiments, the individual is a non-human. In some embodiments, an individual suffers from a respiratory infection. In some embodiments, the individual is in need of treatment.

The terms "polypeptide" and "protein" are used interchangeably to refer to a polymer of amino acid residues and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present application, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, a "neutralizing antibody" refers to an antibody that defends a host cell from an infectious agent by neutralizing any effect (e.g., cytotoxicity) it has biologically.

The term "chimeric protein" refer to a protein in which at least a portion of the polypeptide is derived from a protein that is different from where another portion of the polypeptide is derived from.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity and no more than 100% identity with the native sequence polypeptide after aligning the sequences and introducing gaps, if necessary, to achieve the maximum percent sequence identity. Such variants include, for instance, polypeptides wherein one or more amino acid residues are added, or deleted, at the N- or C-terminus of the polypeptide. In some embodiments, a variant has at least about 80% amino acid sequence identity. In some embodiments, a variant has at least about 90% amino acid sequence identity. In some embodiments, a variant has at least about 95% amino acid sequence identity with the native sequence polypeptide.

As used herein, "Percent (%) amino acid sequence identity" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6 ® cells (Crucell), and 293 and CHO cells, and their derivatives, such as 293-6E and DG44 cells, respectively.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "an," and "the" include plural referents unless the context clearly dictates otherwise.

II. Method of Vaccine Boostering

The present application in one aspect provides a method of boostering the effect of a SARS-CoV-2 vaccine. In some embodiments, there is provided a method of enhancing the effect of a vaccine against SARS-CoV-2 in an individual who has been vaccinated, comprising administering to the individual an effective amount of the vaccine booster composition, wherein the vaccine booster composition comprises a spike protein ("S protein") or a fragment thereof, and optionally wherein the recombinant protein is administered intranasally.

The spike protein described herein may be derived from a coronavirus, such as but not limited to Sarbecovirus. Coronaviruses are a group of related viruses that cause diseases in mammals and birds. In particular, severe acute respiratory syndrome-related coronavirus (SARS-CoV) is a strain of coronavirus that naturally infects humans, bats, and several other mammals. SARS-CoV is an enveloped positive-sense, single-stranded RNA virus that enters its host cell by binding to the ACE2 receptor, and is a member of the genus Betacoronavirus and subgenus Sarbecoronavirus (Sarbecovirus). Coronaviruses (including Sarbecoviruses) are large pleomorphic spherical particles with bulbous surface projections. The average diameter of the virus particles is around 120 nm (0.12 μm). The diameter of the envelope is ~80 nm (0.08 μm) and the spikes are ~20 nm (0.02 μm) long. The viral envelope consists of a lipid bilayer where the membrane (M), envelope (E) and spike (S) structural proteins are anchored. A subset of coronaviruses (specifically the members of betacoronavirus subgroup A) also have a shorter spike-like surface protein called hemagglutinin esterase (HE). Inside the envelope, there is the nucleocapsid, which is formed from multiple copies of the nucleocapsid (N) protein, which are bound to the positive-sense single-stranded RNA genome in a continuous beads-on-a-string type conformation. The lipid bilayer envelope, membrane proteins, and nucleocapsid protect the virus when it is outside the host cell.

A naturally occurring spike protein of a coronavirus forms homotrimers protruding from the viral surface. The S protein comprises two functional subunits responsible for binding to the host cell receptor (S1 subunit) and fusion of the viral and cellular membranes (S2 subunit). For many CoVs, S is cleaved at the boundary between the S1 and S2 subunits, which remain non-covalently bound in the prefusion conformation. The distal S1 subunit comprises the receptor-binding domain(s) and contributes to stabilization of the prefusion state of the membrane-anchored S2 subunit that contains the fusion machinery. For all CoVs, S is further cleaved by host proteases at the so-called S2' site located immediately upstream of the fusion peptide. This cleavage has been proposed to activate the protein for membrane fusion via extensive irreversible conformational changes. As a result, coronavirus entry into susceptible cells is a complex process that requires the concerted action of receptor-binding and proteolytic processing of the S protein to promote virus-cell fusion. See, Walls et al., Cell 180, 281-292, 2020.

For example, the S protein of SARS-CoV could be cleaved by trypsin at two distinct sites, one located at the boundary of S1 and S2, the "classical" S1/S2 site (R667 P1 residue), and the S2' site (R797 P1 residue). Protease cleavage of SARS-CoV S is thought to be sequential, with the S1/S2 cleavage occurring first and enhancing subsequent cleavage at S2'. It is the second cleavage event, at S2', that is believed to be crucial for fusion activation of S. The S 1/S2 cleavage appears dispensable for syncytia formation and virus-cell fusion. See, Millet 2015, Virus Research 202: 120-134.

The spike protein of SARS-CoV-2 can be cleaved by both furin at the S1/S2 site and the transmembrane protease/serine (TMPRSS) protease 2, TMPRSS2, at the S2' site. See, Hoffman et al., Cell 181, 271-280, 2020. The furin cleavage site of SARS-CoV-2 locates between amino acids 685 and 686 of the S protein. SARS-CoV-2 and SARS-CoV both use ACE2 as the receptor to enter human cells. See, Zhou et al., Nature 579: 270, 2020.

S1 of the spike protein can be further divided into an N-terminal domain (NTD) and a C-terminal domain (CTD), both of which can function as a receptor-binding entity (e.g., SARS-CoV and MERS-CoV utilize the S1 CTD to recognize the receptor (also called receptor binding domain [RBD]) (Li et al., 2005, Science 309(5742):1864-8; Lu et al., Nature, 500: 227-231, 2013).

SARS-CoV-2 S protein includes a signaling peptide (amino acid residues 1-19), S1 region containing a NTD (amino acid residues 20-286) and a CTD (amino acid residues 319-541), a S2 region (amino acid residues 686-1213), a transmembrane region (amino acid residues 1214-1236), and a short cytoplasmic domain (amino acid residues 1237-1273). The CTD, in particular amino acid residues 333-527, play key roles in binding to ACE2. In particular, amino acid residues A475, K417, G446, Y449, G496, Q498, T500, G502, Y489, F486, and N487 contribute to binding of the SARS-CoV-2 CTD with hACE2. See, Wang et al., 2020, Cell 181, 1-11, which is incorporated herein by reference in its entirety.

In some embodiments, the vaccine booster composition comprises S protein of SARS-CoV-2 lineage A (SEQ ID NO:1) or a fragment thereof. In some embodiments, the vaccine booster protein comprises an S protein fragment comprising amino acids 200-700, 250-650, 300-600, or 306-541 of SEQ ID NO:1. In some embodiments, the S protein fragment comprises any of 200, 220, 240, 260, 280, 300, 400, 450, or 500 amino acids of SEQ ID NO:1.

In some embodiments, the vaccine booster composition comprises S protein of the omicron variant of SARS-CoV-2 (SARS-CoV-2 lineage B.1.1.529) (SEQ ID NO:2). In some embodiments, the vaccine booster protein comprises an S protein fragment comprising amino acids 200-700, 250-650, 300-600, or 303-538 of SEQ ID NO:2. In some embodiments, the S protein fragment comprises any of 200, 220, 240, 260, 280, 300, 400, 450, or 500 amino acids of SEQ ID NO:2.

In some embodiments, the vaccine booster composition comprises a chimeric protein comprising a spike protein or a fragment thereof. Chimeric proteins that can be used in the methods described herein are further discussed in Section III below.

The vaccine booster compositions described herein can further comprise one or more other components such as an adjuvant. For example, in some embodiments, the vaccine booster composition can further comprise an adjuvant selected from the group consisting of a nucleic acid, a cytokine, or alum.

In some embodiments, the vaccine booster composition is administered at least 7 days after the administration of the SARS-CoV-2 vaccine. In some embodiments, the vaccine booster composition is administered about any of 4, 5, 6, 7, 8, or 9 weeks after the administration of the SARS-CoV-2 vaccine.

In some embodiments, the individual has been administered with at least one dose of the SARS-CoV-2 vaccine. In some embodiments, the individual has been administered with at least two doses of the SARS-CoV-2 vaccine. In some embodiments, the SARS-CoV-2 vaccine is an mRNA-based vaccine, a recombinant virus-based vaccine (for example adenovirus-based vaccine), an inactivated virus-based vaccine (for example an inactivated SARS-CoV-2 vaccine), a subunit vaccine (for example a vaccine comprising an antigenic fragment of a SARS-CoV-2 protein) or a combination thereof. In some embodiments, the vaccine is administered intramuscularly, intranasally, or intradermally.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual has not been exposed to the pathogen. In some embodiments, the individual is diagnosed with SARS-CoV-2. In some embodiments, the individual is at a risk of developing severe symptoms of the infection (e.g., coronavirus infection). In some embodiments, the individual has an underlying medical condition, such as cardiovascular disease, diabetes, chronic respiratory disease, and/or cancer.

III. Chimeric Proteins

The present application in another aspect provides chimeric proteins (such as fusion proteins) comprising: a SARS-CoV-2 spike protein ("S protein") or fragment thereof fused to a booster enhancer domain ("BED"). In some embodiments, the chimeric protein comprises a receptor binding domain ("RBD") of a SARS-CoV-2 spike protein ("S protein") fused to a booster enhancer domain ("BED"). These chimeric protein can be useful for any of the vaccine booster methods described above, or for serving as a vaccine themselves.

The S protein described herein can be the S protein of a wildtype or variant of SARS-CoV-2, including, but not limited to, alpha, beta, delta, or omicron variants of SARS-CoV-2. In some embodiments, the S protein is from SARS-CoV-2 lineage A. In some embodiments, the S protein is from SARS-CoV-2 lineage B.1.1.529. In some embodiments, the S protein is from SARS-CoV-2 lineage B.1.617.2. In some embodiments, the S protein is from SARS-CoV-2 lineage B.1.36.27.

In some embodiments, the RBD is derived from an S protein of SARS-CoV-2 lineage A (SEQ ID NO:1). For example, the RBD in some embodiments comprises amino acids 200-700, 250-650, 300-600, or 306-541 of SEQ ID NO:1. In some embodiments, the RBD comprises amino acids 150-350, 200-400, 250-450, 300-500, 350-550, 400-600, or 450-650 of SEQ ID NO:1. In some embodiments, the RBD comprises any of 200, 220, 240, 260, 280, 300, 400, 450, or 500 amino acids of SEQ ID NO:1.

In some embodiments, the RBD has an amino acid sequence that is about any of 80%, 85%, 90%, 95%, 96%, 97%, 98%, or 99% homologous with amino acids 200-700, 250-650, 300-600, or 306-541 of SEQ ID NO:1. In some embodiments, the RBD has an amino acid sequence that is about any of 80%, 85%, 90%, 95%, 96%, 97%, 98%, or 99% homologous with any of 200, 220, 240, 260, 280, 300, 400, 450, or 500 amino acids of SEQ ID NO:1.

In some embodiments, the RBD comprises a variant of amino acids 200-700, 250-650, 300-600, or 306-541 of SEQ ID NO:1, wherein the variant differs from the parent sequence by no more than about any of 30, 20, 10, 9, 8, 7, 6, 5, 4, 3, 2, or 1 amino acid residues. In some embodiments, the RBD comprises a variant of any of 200, 220, 240, 260, 280, 300, 400, 450, or 500 amino acids of SEQ ID NO:1, wherein the variant differs from the parent sequence by no more than about any of 30, 20, 10, 9, 8, 7, 6, 5, 4, 3, 2, or 1 amino acid residues.

In some embodiments, the RBD is derived from an S protein of the omicron variant of SARS-CoV-2 (SARS-CoV-2 lineage B.1.1.529) (SEQ ID NO:2). For example, the RBD in some embodiments comprises amino acids 200-700, 250-650, 300-600, or 303-538 of SEQ ID NO:2. In some embodiments, the RBD comprises amino acids 150-350, 200-400, 250-450, 300-500, 350-550, 400-600, or 450-650 of SEQ ID NO:2. In some embodiments, the RBD comprises any of 200, 220, 240, 260, 280, 300, 400, 450, or 500 amino acids of SEQ ID NO:2.

In some embodiments, the RBD has an amino acid sequence that is about any of 80%, 85%, 90%, 95%, 96%, 97%, 98%, or 99% homologous with amino acids 200-700, 250-650, 300-600, or 303-538 of SEQ ID NO:2. In some embodiments, the RBD has an amino acid sequence that is about any of 80%, 85%, 90%, 95%, 96%, 97%, 98%, or 99% homologous with any of 200, 220, 240, 260, 280, 300, 400, 450, or 500 amino acids of SEQ ID NO:2.

In some embodiments, the RBD comprises a variant of amino acids 200-700, 250-650, 300-600, or 303-538 of SEQ ID NO:2, wherein the variant differs from the parent sequence by no more than about any of 30, 20, 10, 9, 8, 7, 6, 5, 4, 3, 2, or 1 amino acid residues. In some embodiments, the RBD comprises a variant of any of 200, 220, 240, 260, 280, 300, 400, 450, or 500 amino acids of SEQ ID NO:2, wherein the variant differs from the parent sequence by no more than about any of 30, 20, 10, 9, 8, 7, 6, 5, 4, 3, 2, or 1 amino acid residues.

BED described herein can be any polypeptide that is capable to enhancing the booster function of the RBD. In some embodiments, the BED serves as an adjuvant for the RBD portion of the chimeric protein. In some embodiments, the BED is derived from a protein on a virus, such as a coronavirus, for example a SARS-CoV-2 virus. Suitable proteins from which the BED can be derived from include, but is not limited to, the S protein, the N protein, and the M protein. In some embodiments the BED is about any of 100, 150, 200, or 250 amino acids long.

In some embodiments, the BED is derived from a nucleocapsid protein of a coronavirus. In some embodiments, the BED is derived from the N protein of a SARS-CoV-2 virus (SEQ ID NO:3). For example, the BED in some embodiments comprises amino acids 20-300, 25-250, or 40-180 of SEQ ID NO:3. In some embodiments, the BED comprises amino acids 44-180 of SEQ ID NO:3. In some embodiments, the BED comprises amino acids 25-125, 50-150, 75-175, 100-200, 125-225, or 150-250 of SEQ ID NO:3. In some embodiments, the BED comprises any of 100, 110, 120, 130, 140, or 150 amino acids of SEQ ID NO:3.

In some embodiments, the BED has an amino acid sequence that is about any of 80%, 85%, 90%, 95%, 96%, 97%, 98%, or 99% homologous with amino acids 20-300, 25-250, 30-200, or 40-180 of SEQ ID NO:3. In some embodiments, the BED has an amino acid sequence that is about any of 80%, 85%, 90%, 95%, 96%, 97%, 98%, or 99% homologous with amino acids 44-180 of SEQ ID NO:3. In some embodiments, the BED has an amino acid sequence that is about any of 80%, 85%, 90%, 95%, 96%, 97%, 98%, or 99% homologous with any of 100, 110, 120, 130, 140, or 150 amino acids of SEQ ID NO:3.

In some embodiments, the BED comprises a variant of amino acids 20-300, 25-250, 30-200, or 40-180 of SEQ ID NO:3, wherein the variant differs from the parent sequence by no more than about any of 30, 20, 10, 9, 8, 7, 6, 5, 4, 3, 2, or 1 amino acid residues. In some embodiments, the BED comprises a variant of amino acids 44-180 of SEQ ID NO:3, wherein the variant differs from the parent sequence by no more than about any of 30, 20, 10, 9, 8, 7, 6, 5, 4, 3, 2, or 1 amino acid residues. In some embodiments, the RBD comprises a variant of any of 100, 110, 120, 130, 140, or 150 amino acids of SEQ ID NO:3, wherein the variant differs from the parent sequence by no more than about any of 30, 20, 10, 9, 8, 7, 6, 5, 4, 3, 2, or 1 amino acid residues.

In some embodiments, the RBD is fused directly to the BED. In some embodiments, the RDB is fused to the BED via a peptide linker. In some embodiments, the linker is about 1 to 20 amino acid residues. In some embodiments, the linker is a glycine-serine linker. In some embodiments, the linker has the amino acid sequence of GGGGS.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids (aa) long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 aa to about aa, about 1 aa to about 20 aa, about 1 aa to about 30 aa, about 5 aa to about 15 aa, about 10 aa to about 25 aa, about 5 aa to about 30 aa, about 10 aa to about 30 aa, or about 30 aa to about 50 aa.

In some embodiments, the peptide linker is a flexible linker. Exemplary flexible linkers include glycine polymers $(G)_n$, glycine-serine polymers (including, for example, $(GS)_n$, $(GSGGS)_n$, $(GGGGS)_n$, and $(GGGS)_n$, where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine and is much less restricted than residues with longer side chains (see Scheraga, Rev. Computational Chem. 11 173-142 (1992)). The ordinarily skilled artisan will recognize that design of a fusion protein can include linkers that are all or partially flexible, such that the linker can include a flexible linker portion as well as one or more portions that confer less flexible structure to provide a desired fusion protein structure.

Natural linkers adopt various conformations in secondary structure, such as helical, β-strand, coil/bend and turns, to exert their functions. Linkers in an ci-helix structure might serve as rigid spacers to effectively separate protein domains, thus reducing their unfavorable interactions. Non-helical linkers with Pro-rich sequence could increase the linker rigidity and function in reducing inter-domain interference.

In some embodiments, the RBD is fused to the N-terminus of the BED. In some embodiments, the RBD is fused to the C-terminus of the BED. In some embodiments, the chimeric protein comprises multiple RBD and/or BED, for example multiple RBD and/or BED arranged in tandem.

In some embodiments, the chimeric protein comprises an amino acid sequence that is about any of 80%, 85%, 90%, 95%, 96%, 97%, 98%, or 99% homologous with SEQ ID NO:4. In some embodiments, the chimeric protein comprises a variant of the amino acid sequence of SEQ ID NO:4, wherein the variant differs from the parent sequence by no more than about any of 50, 40, 30, 20, 10, 9, 8, 7, 6, 5, 4, 3, 2, or 1 amino acid residues. In some embodiments, the chimeric protein comprises the amino acid sequence of SEQ ID NO:4.

In some embodiments, the chimeric protein comprises an amino acid sequence that is about any of 80%, 85%, 90%, 95%, 96%, 97%, 98%, or 99% homologous with SEQ ID NO:5. In some embodiments, the chimeric protein comprises a variant of the amino acid sequence of SEQ ID NO:5, wherein the variant differs from the parent sequence by no more than about any of 50, 40, 30, 20, 10, 9, 8, 7, 6, 5, 4, 3, 2, or 1 amino acid residues. In some embodiments, the chimeric protein comprises the amino acid sequence of SEQ ID NO:5.

IV. Vaccine or Vaccine Booster Composition

The present application in some embodiments provides a vaccine or a vaccine booster composition comprising any of the chimeric proteins described herein.

In some embodiments according to any one of the methods or compositions described herein, the vaccine or vaccine booster composition does not comprise an adjuvant. In some embodiments according to any one of the methods or compositions described herein, the vaccine or vaccine booster composition does not comprise liquid nanoparticles (LNP). In some embodiments, an individual receiving the vaccine or vaccine booster composition without adjuvant exhibits reduced incidence of adverse effects associated with an adjuvant, such as but not limited to allergy, irritation, inflammation, pain, tenderness, redness, cell toxicity, or adenopathy at the administration site or at a proximal or distal site, as compared to a corresponding vaccine or vaccine booster comprising an adjuvant. In some embodiments, the vaccine or vaccine booster composition is for use in intranasal administration, wherein an individual receiving the vaccine or vaccine booster composition without adjuvant exhibits reduced allergy or irritation to the mucosa as compared to a corresponding vaccine or vaccine booster comprising an adjuvant.

The vaccine booster compositions described herein can further comprise one or more of other components such as an adjuvant. For example, in some embodiments, the vaccine booster composition can further comprise an adjuvant selected from the group consisting of a nucleic acid, a cytokine, or alum.

The vaccine or vaccine booster compositions described herein may comprises a single type of chimeric protein. In some embodiments, vaccine or vaccine booster compositions comprises a plurality (e.g., 2, 3, 4, 5, 6, 7, 8, 9, 10, 15, 20, or more) of different chimeric proteins.

In some embodiments, the vaccine or vaccine booster composition is formulated for topical administration to a mucosa, such as nasal mucosa, larynx mucosa, trachea mucosa, bronchi mucosa, lung mucosa, eye mucosa, and combinations thereof. In some embodiments, the vaccine or vaccine booster composition is formulated for administration via a nasal spray, an inhaler, a nebulizer, or an eye drop. In some embodiments, the vaccine or vaccine booster composition is formulated for intranasal administration.

V. Methods of Treatment

The present application further provides methods of preventing or treating an infection caused by a pathogen (such as SARS-CoV-2), comprising administering to the individual an effective amount of any one of the chimeric proteins described herein.

In some embodiments, the chimeric protein is administered to the individual before the individual is exposed to the pathogen. In some embodiments, the chimeric protein is administered to the individual within about 7 days or less (such as but not limited to any one of 7 days, 6 days, 5 days, 4 days, 72 hours, 48 hours, or less) from exposure of the individual to the pathogen. In some embodiments, the chimeric protein is administered via a nasal spray, an inhaler, a nebulizer, or an eye drop.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual has not been exposed to the pathogen (such as SARS-CoV-2). In some embodiments, the individual is diagnosed with SARS-CoV-2. In some embodiments, the individual had been diagnosed with SARS-CoV-2. In some embodiments, the individual had been infected with one or more strains of SARS-CoV-2. In some embodiments, the individual had been infected with one or more strains of SARS-CoV-2 and has developed natural immunity against the one or more strains of SARS-CoV-2. In some embodiments, the individual had been infected with one or more of lineage A, lineage B.1.1.529, and/or lineage B.1.617.2 strains of SARS-CoV-2. In some embodiments, the individual had been infected with one or more of alpha, beta, D614G, delta, omicron BA.1, omicron BA.1.1, omicron BA.2, and/or omicron BA.3 strains of SARS-CoV-2. In some embodiments, the individual is at a risk of developing severe symptoms of the infection (e.g., coronavirus infection). In some embodiments, the individual has an underlying medical condition, such as cardiovascular disease, diabetes, chronic respiratory disease, and/or cancer. In some embodiments, the individual has a compromised immune system. In some embodiments, the individual has a compromised adaptive immune system and/or a compromised innate immune system. In some embodiments, the individual has a weakened immune system. In some embodiments, the individual has a weakened adaptive immune system and/or a weakened innate immune system. In some embodiments, the individual is administered one or more courses of immunosuppresants. In some embodiments, the individual had been administered one or more courses of immunosuppresants.

In some embodiments, the chimeric protein is administered as a single agent, or in combination with a second, third, or fourth agent (including, e.g., anti-viral drugs, convalescent plasma, anti-inflammatory drugs etc.) to treat the infection.

Efficacy of the treatments can be evaluated, for example, by viral load (e.g., via detection of viral DNA), duration of survival, quality of life, viral protein expression and/or activity, detection of serological antibodies against the coronavirus, assessment of respiratory functions, and/or Computerized Tomography (CT) imaging Efficacy of the a vaccine or vaccine booster can be evaluated, for example, by levels of neutralizing antibodies against one or more proteins of the respiratory virus (such as SARS-CoV-2) in serum or other bodily fluid (such as but not limited to bronchoalveolar lavage fluids), or by the neutralizing activity of serum or other bodily fluid against one or more strains of the respiratory virus (such as SARS-CoV-2).

In some embodiments, wherein the method comprises administrating to the individual an effective amount of any one of the chimeric proteins described herein, the individual displays increased neutralizing antibody level in serum against SARS-CoV-2 spike RBD (receptor binding domain of spike protein) as compared to before administration of the chimeric protein. In some embodiments, the individual displays increased neutralizing antibody level in serum against SARS-CoV-2 lineage A spike RBD as compared to before administration of the chimeric protein. In some embodiments, the individual displays increased neutralizing antibody level in serum against SARS-CoV-2 lineage B.1.1.529 spike RBD as compared to before administration of the chimeric protein. In some embodiments, the individual displays increased neutralizing antibody level in serum against SARS-CoV-2 lineage B.1.617.2 spike RBD as compared to before administration of the chimeric protein. In some embodiments, the individual displays increased neutralizing antibody level in serum against a SARS-CoV-2 variant spike RBD as compared to before administration of the chimeric protein. In some embodiments according to any one of the methods described herein, the individual displays an increase in the neutralizing antibody level by about any one of 10%, 20%, 50%, 75%, 100%, 2-fold, 5-fold, 10-fold, 25-fold, 50-fold, 100-fold, 500-fold, or 1000-fold or more, as compared to before administration of the chimeric protein. In some embodiments, the individual had been previously administered with at least one dose (such as one, two, three or more doses) of a SARS-CoV-2 vaccine. In some embodiments, the individual had been previously infected with one or more strains of SARS-CoV-2. In some embodiments, the neutralizing antibody level is determined at about any one of 1, 7, 14, 21, 30, 45, 60, 90, 120, 180, 240, 360, 480, or 720 days after administration of the chimeric protein.

In some embodiments, wherein the method comprises administrating to the mucosa of the individual an effective amount of any one of the chimeric proteins described herein, the individual displays increased mucosal immunity against SARS-CoV-2 as compared to before administration of the chimeric protein. In some embodiments, the individual displays induction of lung resident memory B cells subsequent to administration of the chimeric protein. In some embodiments, the individual displays induction of follicular helper T cells subsequent to administration of the chimeric protein. In some embodiments, the individual displays increased neutralizing antibody level in bronchoalveolar lavage (BAL) fluids against SARS-CoV-2 lineage A spike RBD as compared to before administration of the chimeric protein. In some embodiments, the individual displays increased neutralizing antibody level in BAL fluids against SARS-CoV-2 lineage B.1.1.529 spike RBD as compared to before administration of the chimeric protein. In some embodiments, the individual displays increased neutralizing antibody level in BAL fluids against SARS-CoV-2 lineage B.1.617.2 spike RBD as compared to before administration of the chimeric protein. In some embodiments, the individual displays increased neutralizing antibody level in BAL fluids against a SARS-CoV-2 variant spike RBD as compared to before administration of the chimeric protein. In some embodiments, the neutralizing antibody comprises IgA. In some embodiments according to any one of the methods described herein, the individual displays an increase in the neutralizing antibody level by about any one of 10%, 20%, 50%, 75%, 100%, 2-fold, 5-fold, 10-fold, 25-fold, 50-fold, 100-fold, 500-fold, or 1000-fold or more, as compared to before administration of the chimeric protein. In some embodiments, the individual had been previously administered with at least one dose (such as one, two, three or more doses) of a SARS-CoV-2 vaccine. In some embodiments, the individual had been previously infected with one or more strains of SARS-CoV-2. In some embodiments, the neutralizing antibody level is determined at about any one of 1, 7, 14, 21, 30, 60, 90, 120, 180, 240, 360, 480, or 720 days after administration of the chimeric protein.

In some embodiments, wherein the method comprises administrating to the individual an effective amount of any one of the chimeric proteins described herein, the individual displays increased neutralizing activity in serum against SARS-CoV-2 as compared to before administration of the chimeric protein. In some embodiments, the individual displays increased neutralizing activity in serum against SARS-CoV-2 lineage A as compared to before administration of the chimeric protein. In some embodiments, the individual displays increased neutralizing activity in serum against SARS-CoV-2 lineage B.1.1.529 as compared to before administration of the chimeric protein. In some embodiments, the individual displays increased neutralizing activity in serum against SARS-CoV-2 lineage B.1.617.2 as compared to before administration of the chimeric protein. In some embodiments, the individual displays increased neutralizing activity in serum against a SARS-CoV-2 variant as compared to before administration of the chimeric protein. In some embodiments, the neutralizing activity is quantitatively determined by focus reduction neutralization assay against the virus strain. In some embodiments according to any one of the methods described herein, the individual displays an increase in the neutralizing activity by about any one of 10%, 20%, 50%, 75%, 100%, 2-fold, 5-fold, 10-fold, 25-fold, 50-fold, 100-fold, 500-fold, or 1000-fold or more, as compared to before administration of the chimeric protein. In some embodiments, the individual had been previously administered with at least one dose (such as one, two, three or more doses) of a SARS-CoV-2 vaccine. In some embodiments, the individual had been previously infected with one or more strains of SARS-CoV-2. In some embodiments, the neutralizing activity is determined at about any one of 1, 7, 14, 21, 30, 45, 60, 90, 120, 180, 240, 360, 480, or 720 days after administration of the chimeric protein.

In some embodiments, wherein the method comprises administrating to the mucosa of the individual an effective amount of any one of the chimeric proteins described herein, the individual displays increased mucosal immunity against SARS-CoV-2 as compared to before administration of the chimeric protein. In some embodiments, the individual displays increased neutralizing activity in bronchoalveolar lavage fluids (BAL) fluids against SARS-CoV-2 lineage A as compared to before administration of the chimeric protein. In some embodiments, the individual displays increased neutralizing activity in BAL fluids against SARS-CoV-2 lineage B.1.1.529 as compared to before administration of the chimeric protein. In some embodiments, the individual displays increased neutralizing activity in BAL fluids against SARS-CoV-2 lineage B.1.617.2 as compared to before administration of the chimeric protein. In some embodiments, the individual displays increased neutralizing activity in BAL fluids against a SARS-CoV-2 variant as compared to before administration of the chimeric protein. In some embodiments, the neutralizing activity is quantitatively determined by focus reduction neutralization assay against the authentic live virus. In some embodiments according to any one of the methods described herein, the individual displays an increase in the neutralizing activity by about any one of 10%, 20%, 50%, 75%, 100%, 2-fold, 5-fold, 10-fold, 25-fold, 50-fold, 100-fold, 500-fold, or 1000-fold or more, as compared to before administration of the chimeric protein. In some embodiments, the individual had been previously administered with at least one dose (such as one, two, three or more doses) of a SARS-CoV-2 vaccine. In some embodiments, the individual had been previously infected with one or more strains of SARS-CoV-2. In some embodiments, the neutralizing activity is determined at about any one of 1, 7, 14, 21, 30, 45, 60, 90, 120, 180, 240, 360, 480, or 720 days after administration of the chimeric protein.

In some embodiments, wherein the method comprises administrating to the individual an effective amount of any one of the chimeric proteins described herein, wherein the chimeric protein comprises a sequence derived from SARS-CoV-2 lineage B.1.1.529 spike RBD, the individual displays increased or similar neutralizing antibody level in serum against SARS-CoV-2 spike RBD (receptor binding domain of spike protein) as compared to a corresponding individual receiving administration of a vaccine derived from SARS-CoV-2 lineage A spike protein (such as but not limited to an mRNA vaccine or a subunit vaccine). In some embodiments, the individual displays increased or similar neutralizing antibody level in serum against SARS-CoV-2 lineage B.1.1.529 spike RBD as compared to a corresponding individual receiving administration of a vaccine derived from SARS-CoV-2 lineage A spike protein. In some embodiments, the individual displays increased or similar neutralizing antibody level in serum against SARS-CoV-2 lineage A spike RBD as compared to a corresponding individual receiving administration of a vaccine derived from SARS- CoV-2 lineage A spike protein. In some embodiments, the individual displays increased or similar neutralizing antibody level in serum against SARS-CoV-2 lineage B.1.617.2 spike RBD as compared to a corresponding individual receiving administration of a vaccine derived from SARS-CoV-2 lineage A spike protein. In some embodiments, the individual displays increased or similar neutralizing antibody level in serum against a SARS-CoV-2 variant spike RBD as compared to a corresponding individual receiving administration of a vaccine derived from SARS-CoV-2 lineage A spike protein. In some embodiments according to any one of the methods described herein, the individual administered with the chimeric protein displays an increase in the neutralizing antibody level by about any one of 10%, 20%, 50%, 75%, 100%, 2-fold, 5-fold, 10-fold, 25-fold, 50-fold, 100-fold, 500-fold, or 1000-fold or more, as compared to a corresponding individual receiving administration of a vaccine derived from SARS-CoV-2 lineage A spike protein. In some embodiments, the individual had been previously administered with at least one dose (such as one, two, three or more doses) of a SARS-CoV-2 vaccine. In some embodiments, the individual had been previously infected with one or more strains of SARS-CoV-2. In some embodiments, the neutralizing antibody level is determined at about any one of 1, 7, 14, 21, 30, 45, 60, 90, 120, 180, 240, 360, 480, or 720 days after administration of the chimeric protein or the vaccine derived from SARS-CoV-2 lineage A spike protein.

In some embodiments, wherein the method comprises administrating to the mucosa of the individual an effective amount of any one of the chimeric proteins described herein, wherein the chimeric protein comprises a sequence derived from SARS-CoV-2 lineage B.1.1.529 spike RBD, the individual displays increased or similar mucosal immunity against SARS-CoV-2 spike RBD as compared to a corresponding individual receiving administration of a vaccine derived from SARS-CoV-2 lineage A spike protein (such as but not limited to an mRNA vaccine or a subunit vaccine). In some embodiments, the individual displays increased or similar neutralizing antibody level in BAL fluids against SARS-CoV-2 lineage B.1.1.529 spike RBD as compared to a corresponding individual receiving administration of a vaccine derived from SARS-CoV-2 lineage A spike protein. In some embodiments, the individual displays increased or similar neutralizing antibody level in BAL fluids against SARS-CoV-2 lineage A spike RBD as compared to a corresponding individual receiving administration of a vaccine derived from SARS-CoV-2 lineage A spike protein. In some embodiments, the individual displays increased or similar neutralizing antibody level in BAL fluids against SARS-CoV-2 lineage B.1.617.2 spike RBD as compared to a corresponding individual receiving administration of a vaccine derived from SARS-CoV-2 lineage A spike protein. In some embodiments, the individual displays increased or similar neutralizing antibody level in BAL fluids against a SARS-CoV-2 variant spike RBD as compared to a corresponding individual receiving administration of a vaccine derived from SARS-CoV-2 lineage A spike protein. In some embodiments, the neutralizing antibody comprises IgA. In some embodiments according to any one of the methods described herein, the individual administered with the chimeric protein displays an increase in the neutralizing antibody level by about any one of 10%, 20%, 50%, 75%, 100%, 2-fold, 5-fold, 10-fold, 25-fold, 50-fold, 100-fold, 500-fold, or 1000-fold or more, as compared to a corresponding individual receiving administration of a vaccine derived from SARS-CoV-2 lineage A spike protein. In some embodiments, the individual had been previously administered with at least one dose (such as one, two, three or more doses) of a SARS-CoV-2 vaccine. In some embodiments, the individual had been previously infected with one or more strains of SARS-CoV-2. In some embodiments, the neutralizing antibody level is determined at about any one of 1, 7, 14, 21, 30, 45, 60, 90, 120, 180, 240, 360, 480, or 720 days after administration of the chimeric protein or the vaccine derived from SARS-CoV-2 lineage A spike protein.

In some embodiments, wherein the method comprises administrating to the individual an effective amount of any one of the chimeric proteins described herein, wherein the chimeric protein comprises a sequence derived from SARS-CoV-2 lineage B.1.1.529 spike RBD, the individual displays increased or similar neutralizing activity in serum against SARS-CoV-2 as compared to a corresponding individual receiving administration of a vaccine derived from SARS-CoV-2 lineage A spike protein (such as but not limited to an mRNA vaccine or a subunit vaccine). In some embodiments, the individual displays increased or similar neutralizing activity in serum against SARS-CoV-2 lineage B.1.1.529 as compared to a corresponding individual receiving administration of a vaccine derived from SARS-CoV-2 lineage A spike protein. In some embodiments, the individual displays increased or similar neutralizing activity in serum against SARS-CoV-2 lineage A as compared to a corresponding individual receiving administration of a vaccine derived from SARS-CoV-2 lineage A spike protein. In some embodiments, the individual displays increased or similar neutralizing activity in serum against SARS-CoV-2 lineage B.1.617.2 as compared to a corresponding individual receiving administration of a vaccine derived from SARS-CoV-2 lineage A spike protein. In some embodiments, the individual displays increased or similar neutralizing activity in serum against a SARS-CoV-2 variant spike RBD as compared to a corresponding individual receiving administration of a vaccine derived from SARS-CoV-2 lineage A spike protein. In some embodiments, the neutralizing activity is quantitatively determined by focus reduction neutralization assay against the virus strain. In some embodiments according to any one of the methods described herein, the individual administered with the chimeric protein displays an increase in the neutralizing activity by about any one of 10%, 20%, 50%, 75%, 100%, 2-fold, 5-fold, 10-fold, 25-fold, 50-fold, 100-fold, 500-fold, or 1000-fold or more, as compared to a corresponding individual receiving administration of a vaccine derived from SARS-CoV-2 lineage A spike protein. In some embodiments, the individual had been previously administered with at least one dose (such as one, two, three or more doses) of a SARS-CoV-2 vaccine. In some embodiments, the individual had been previously infected with one or more strains of SARS-CoV-2. In some embodiments, the neutralizing activity is determined at about any one of 1, 7, 14, 21, 30, 45, 60, 90, 120, 180, 240, 360, 480, or 720 days after administration of the chimeric protein or the vaccine derived from SARS-CoV-2 lineage A spike protein.

In some embodiments, wherein the method comprises administrating to the mucosa of the individual an effective amount of any one of the chimeric proteins described herein, wherein the chimeric protein comprises a sequence derived from SARS-CoV-2 lineage B.1.1.529 spike RBD, the individual displays increased or similar mucosal immunity against SARS-CoV-2 spike RBD as compared to a corresponding individual receiving administration of a vaccine derived from SARS-CoV-2 lineage A spike protein (such as but not limited to an mRNA vaccine or a subunit vaccine).

In some embodiments, the individual displays increased or similar neutralizing activity in BAL fluids against SARS-CoV-2 lineage B.1.1.529 spike RBD as compared to a corresponding individual receiving administration of a vaccine derived from SARS-CoV-2 lineage A spike protein. In some embodiments, the individual displays increased or similar neutralizing activity in BAL fluids against SARS-CoV-2 lineage A spike RBD as compared to a corresponding individual receiving administration of a vaccine derived from SARS-CoV-2 lineage A spike protein. In some embodiments, the individual displays increased or similar neutralizing activity in BAL fluids against SARS-CoV-2 lineage B.1.617.2 spike RBD as compared to a corresponding individual receiving administration of a vaccine derived from SARS-CoV-2 lineage A spike protein. In some embodiments, the individual displays increased or similar neutralizing activity in BAL fluids against a SARS-CoV-2 variant spike RBD as compared to a corresponding individual receiving administration of a vaccine derived from SARS-CoV-2 lineage A spike protein. In some embodiments, the neutralizing activity is quantitatively determined by focus reduction neutralization assay against authentic live virus. In some embodiments according to any one of the methods described herein, the individual administered with the chimeric protein displays an increase in the neutralizing activity by about any one of 10%, 20%, 50%, 75%, 100%, 2-fold, 5-fold, 10-fold, 25-fold, 50-fold, 100-fold, 500-fold, or 1000-fold or more, as compared to a corresponding individual receiving administration of a vaccine derived from SARS-CoV-2 lineage A spike protein. In some embodiments, the individual had been previously administered with at least one dose (such as one, two, three or more doses) of a SARS-CoV-2 vaccine. In some embodiments, the individual had been previously infected with one or more strains of SARS-CoV-2. In some embodiments, the neutralizing activity is determined at about any one of 1, 7, 14, 21, 30, 45, 60, 90, 120, 180, 240, 360, 480, or 720 days after administration of the chimeric protein or the vaccine derived from SARS-CoV-2 lineage A spike protein.

In some embodiments, wherein the method comprises administrating to the individual an effective amount of any one of the chimeric proteins described herein, the individual displays increased neutralizing antibody level in serum against the booster-enhanced domain (BED) as compared to before administration of the chimeric protein. In some embodiments, the individual displays increased neutralizing antibody level in BAL fluids against the booster-enhanced domain (BED) as compared to before administration of the chimeric protein. In some embodiments according to any one of the methods described herein, the individual displays an increase in the neutralizing antibody level by about any one of 10%, 20%, 50%, 75%, 100%, 2-fold, 5-fold, 10-fold, 25-fold, 50-fold, 100-fold, 500-fold, or 1000-fold or more, as compared to before administration of the chimeric protein. In some embodiments, the individual had been previously administered with at least one dose (such as one, two, three or more doses) of a SARS-CoV-2 vaccine. In some embodiments, the individual had been previously infected with one or more strains of SARS-CoV-2. In some embodiments, the individual has not been exposed to SARS-CoV-2. In some embodiments, the BED is derived from a protein of a SARS-CoV-2 virus. In some embodiments, the BED is derived from the N protein of a SARS-CoV-2 virus.

VI. Nucleic Acids and Methods of Preparation

Nucleic acid molecules encoding the chimeric proteins thereof described herein are contemplated. Nucleic acid molecules may be constructed using recombinant DNA techniques conventional in the art. In some embodiments, a nucleic acid molecule is an expression vector that is suitable for expression in a selected host cell.

Vectors comprising polynucleotides that encode the chimeric proteins described herein are also provided. Such vectors include, but are not limited to, DNA vectors, phage vectors, viral vectors, retroviral vectors, etc.

In various embodiments, the chimeric proteins may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6 ® cells (Crucell); and NSO cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

The invention also provides host cells comprising any of the nucleic acids or vectors described herein. In some embodiments, the invention provides a host cell comprising a chimeric protein described herein. Non-limiting examples of mammalian host cells include but not limited to COS, HeLa, and CHO cells. Suitable non-mammalian host cells include prokaryotes (such as *E. coli* or *B. subtillis*) and yeast (such as *S. cerevisae, S. pombe*; or *K lactis*).

The chimeric proteins may be purified by any suitable method. Such methods include, but are not limited to, the use of affinity matrices or hydrophobic interaction chromatography. Ion exchange chromatography (e.g. anion exchange chromatography and/or cation exchange chromatography) and mixed-mode chromatography (e.g. reversed phase/anion exchange, reversed phase/cation exchange, hydrophilic interaction/anion exchange, hydrophilic interaction/cation exchange, etc.) may also suitable for purifying the chimeric proteins described herein.

VII. Kits and Articles of Manufacture

In some embodiments, there is provided an article of manufacture comprising the vaccine or vaccine booster compositions useful for the prevention or treatment of a microbial infection (e.g., infection by SARS-CoV-2) or for boostering a SARS-CoV-2 vaccine. The article of manufacture can comprise a container and a label or package insert on or associated with the container. Suitable containers include, for example, bottles, vials, syringes, etc. The containers may be formed from a variety of materials such as glass or plastic. Generally, the container holds a composition, which is effective for treating a microbial infection, described herein, and may have a sterile access port. In some embodiments, the article of manufacture is a nasal spray, an inhaler, a nebulizer, or an eye drop. Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a microbial infection. In some embodiments, the package insert indicates that the composition is used for treating and/or preventing a viral infection. In some embodiments, the package insert indicates that the composition is used for reducing severity in symptoms, hospitalization and/or death upon a viral infection. The label or package insert may further comprise instructions for administering the composition to a patient.

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits of the invention include one or more containers comprising any one of the compositions described herein (or unit dosage form and/or article of manufacture). In some embodiments, the kit further comprises other agents and/or instructions for use in accordance with any of the methods described herein. The kit may further comprise a description of selection of individuals suitable for prevention or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The containers may be unit doses, bulk packages (e.g., multi-dose packages) or sub-unit doses. Kits may also include multiple unit doses of the pharmaceutical compositions and instructions for use and packaged in quantities sufficient for storage and use in pharmacies, for example, hospital pharmacies and compounding pharmacies.

VIII. Sequences of Proteins Described Herein

| SEQ ID | Description | Sequence |
|---|---|---|
| 1 | S protein of SARS-COV-2 lineage A | MFVFLVLLPLVSSQCVNLTTRTQLPPAYTNSFTRGVYYPDKV<br>FRSSVLHSTQDLFLPFFSNVTWFHAIHVSGTNGTKRFDNPVL<br>PFNDGVYFASTEKSNIIRGWIFGTTLDSKTQSLLIVNNATNV<br>VIKVCEFQFCNDPFLGVYYHKNNKSWMESEFRVYSSANNCTF<br>EYVSQPFLMDLEGKQGNFKNLREFVFKNIDGYFKIYSKHTPI<br>NLVRDLPQGFSALEPLVDLPIGINITRFQTLLALHRSYLTPG<br>DSSSGWTAGAAAYYVGYLQPRTFLLKYNENGTITDAVDCALD<br>PLSETKCTLKSFTVEKGIYQTSNFRVQPTESIVRFPNITNLC<br>PFGEVFNATRFASVYAWNRKRISNCVADYSVLYNSASFSTFK<br>CYGVSPTKLNDLCFTNVYADSFVIRGDEVRQIAPGQTGKIAD<br>YNYKLPDDFTGCVIAWNSNNLDSKVGGNYNYLYRLFRKSNLK<br>PFERDISTEIYQAGSTPCNGVEGENCYFPLQSYGFQPTNGVG<br>YQPYRVVVLSFELLHAPATVCGPKKSTNLVKNKCVNFNFNGL<br>TGTGVLTESNKKFLPFQQFGRDIADTTDAVRDPQTLEILDIT<br>PCSFGGVSVITPGTNTSNQVAVLYQDVNCTEVPVAIHADQLT<br>PTWRVYSTGSNVFQTRAGCLIGAEHVNNSYECDIPIGAGICA<br>SYQTQTNSPRRARSVASQSIIAYTMSLGAENSVAYSNNSIAI<br>PTNFTISVTTEILPVSMTKTSVDCTMYICGDSTECSNLLLQY<br>GSFCTQLNRALTGIAVEQDKNTQEVFAQVKQIYKTPPIKDFG<br>GFNFSQILPDPSKPSKRSFIEDLLFNKVTLADAGFIKQYGDC<br>LGDIAARDLICAQKFNGLTVLPPLLTDEMIAQYTSALLAGTI<br>TSGWTFGAGAALQIPFAMQMAYRENGIGVTQNVLYENQKLIA<br>NQFNSAIGKIQDSLSSTASALGKLQDVVNQNAQALNTLVKQL<br>SSNFGAISSVLNDILSRLDKVEAEVQIDRLITGRLQSLQTYV<br>TQQLIRAAEIRASANLAATKMSECVLGQSKRVDFCGKGYHLM<br>SFPQSAPHGVVFLHVTYVPAQEKNFTTAPAICHDGKAHFPRE<br>GVFVSNGTHWFVTQRNFYEPQIITTDNTFVSGNCDVVIGIVN<br>NTVYDPLQPELDSFKEELDKYFKNHTSPDVDLGDISGINASV<br>VNIQKEIDRLNEVAKNLNESLIDLQELGKYEQYIKWPWYIWL<br>GFIAGLIAIVMVTIMLCCMTSCCSCLKGCCSCGSCCKFDEDD<br>SEPVLKGVKLHYT |
| 2 | S protein of SARS-COV-2 lineage B.1.1.529 | MFVFLVLLPLVSSQCVNLTTRTQLPPAYTNSFTRGVYYPDKV<br>FRSSVLHSTQDLFLPFFSNVTWFHVISGTNGTKRFDNPVLPF<br>NDGVYFASIEKSNIIRGWIFGTTLDSKTQSLLIVNNATNVVI<br>KVCEFQFCNDPFLDHKNNKSWMESEFRVYSSANNCTFEYVSQ<br>PFLMDLEGKQGNFKNLREFVFKNIDGYFKIYSKHTPIIVREP<br>EDLPQGFSALEPLVDLPIGINITRFQTLLALHRSYLTPGDSS<br>SGWTAGAAAYYVGYLQPRTFLLKYNENGTITDAVDCALDPLS<br>ETKCTLKSFTVEKGIYQTSNFRVQPTESIVRFPNITNLCPFD<br>EVFNATRFASVYAWNRKRISNCVADYSVLYNLAPFFTFKCYG<br>VSPTKLNDLCFTNVYADSFVIRGDEVRQIAPGQTGNIADYNY<br>KLPDDFTGCVIAWNSNKLDSKVSGNYNYLYRLFRKSNLKPFE<br>RDISTEIYQAGNKPCNGVAGENCYFPLRSYSFRPTYGVGHQP<br>YRVVVLSFELLHAPATVCGPKKSTNLVKNKCVNFNFNGLKGT<br>GVLTESNKKFLPFQQFGRDIADTTDAVRDPQTLEILDITPCS<br>FGGVSVITPGTNTSNQVAVLYQGVNCTEVPVAIHADQLTPTW<br>RVYSTGSNVFQTRAGCLIGAEYVNNSYECDIPIGAGICASYQ<br>TQTKSHRRARSVASQSIIAYTMSLGAENSVAYSNNSIAIPTN<br>FTISVTTEILPVSMTKTSVDCTMYICGDSTECSNLLLQYGSF<br>CTQLKRALTGIAVEQDKNTQEVFAQVKQIYKTPPIKYFGGFN<br>FSQILPDPSKPSKRSFIEDLLFNKVTLADAGFIKQYGDCLGD |

-continued

| SEQ ID | Description | Sequence |
|---|---|---|
| | | IAARDLICAQKFKGLTVLPPLLTDEMIAQYTSALLAGTITSG<br>WTFGAGAALQIPFAMQMAYRFNGIGVTQNVLYENQKLIANQF<br>NSAIGKIQDSLSSTASALGKLQDVVNHNAQALNTLVKQLSSK<br>FGAISSVLNDIFSRLDKVEAEVQIDRLITGRLQSLQTYVTQQ<br>LIRAAEIRASANLAATKMSECVLGQSKRVDFCGKGYHLMSFP<br>QSAPHGVVFLHVTYVPAQEKNFTTAPAICHDGKAHFPREGVF<br>VSNGTHWFVTQRNFYEPQIITTDNTFVSGNCDVVIGIVNNTV<br>YDPLQPELDSFKEELDKYFKNHTSPDVDLGDISGINASVVNI<br>QKEIDRLNEVAKNLNESLIDLQELGKYEQYIKWPWYIWLGFI<br>AGLIAIVMVTIMLCCMTSCCSCLKGCCSCGSCCKFDEDDSEP<br>VLKGVKLHYT |
| 3 | N protein of SARS-COV-2 | MSDNGPQNQRNAPRITFGGPSDSTGSNQNGERSGARSKQRRP<br>QGLPNNTASWFTALTQHGKEDLKFPRGQGVPINTNSSPDDQI<br>GYYRRATRRIRGGDGKMKDLSPRWYFYYLGTGPEAGLPYGAN<br>KDGIIWVATEGALNTPKDHIGTRNPANNAAIVLQLPQGTTLP<br>KGFYAEGSRGGSQASSRSSSRSRNSSRNSTPGSSRGTSPARM<br>AGNGGDAALALLLLDRLNQLESKMSGKGQQQQGQTVTKKSAA<br>EASKKPRQKRTATKAYNVTQAFGRRGPEQTQGNFGDQELIRQ<br>GTDYKHWPQIAQFAPSASAFFGMSRIGMEVTPSGTWLTYTGA<br>IKLDDKDPNFKDQVILLNKHIDAYKTFPPTEPKKDKKKKADE<br>TQALPQRQKKQQTVTLLPAADLDDFSKQLQQSMSSADSTQA |
| 4 | Full length sequence of N-RBD$^{WT}$ | MDAMKRGLCCVLLLCGAVFVSPSAAHHHHHHGGGGSLEVLFQ<br>GPGLPNNTASWFTALTQHGKEDLKFPRGQGVPINTNSSPDDQ<br>IGYYRRATRRIRGGDGKMKDLSPRWYFYYLGTGPEAGLPYGA<br>NKDGIIWVATEGALNTPKDHIGTRNPANNAAIVLQLPQGTTL<br>PKGFYAEGSRGGSFTVEKGIYQTSNFRVQPTESIVRFPNITN<br>LCPFGEVENATRFASVYAWNRKRISNCVADYSVLYNSASFST<br>FKCYGVSPTKLNDLCFTNVYADSFVIRGDEVRQIAPGQTGKI<br>ADYNYKLPDDFTGCVIAWNSNNLDSKVGGNYNYLYRLFRKSN<br>LKPFERDISTEIYQAGSTPCNGVEGENCYFPLQSYGFQPTNG<br>VGYQPYRVVVLSFELLHAPATVCGPKKSTNLVKNKCVNF* |
| 5 | Full length sequence of N-RBD$^{omicron}$ | MDAMKRGLCCVLLLCGAVFVSPSAAHHHHHHGGGGSLEVLFQ<br>GPGLPNNTASWFTALTQHGKEDLKFPRGQGVPINTNSSPDDQ<br>IGYYRRATRRIRGGDGKMKDLSPRWYFYYLGTGPEAGLPYGA<br>NKDGIIWVATEGALNTPKDHIGTRNPANNAAIVLQLPQGTTL<br>PKGFYAEGSRGGSFTVEKGIYQTSNFRVQPTESIVRFPNITN<br>LCPFDEVFNATRFASVYAWNRKRISNCVADYSVLYNLAPFFT<br>FKCYGVSPTKLNDLCFTNVYADSFVIRGDEVRQIAPGQTGNI<br>ADYNYKLPDDFTGCVIAWNSNKLDSKVSGNYNYLYRLFRKSN<br>LKPFERDISTEIYQAGNKPCNGVAGENCYFPLRSYSFRPTYG<br>VGHQPYRVVVLSFELLHAPATVCGPKKSTNLVKNKCVNF* |

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1. Chimeric SARS-CoV-2 Protein (N-RBD$^{WT}$) Elicited Neutralizing Antibodies To address the issue of compromised neutralization against newly emerged SARS-CoV-2 variants and significant decline of neutralizing antibody (nAb) level after 4-6 months of vaccination, a chimeric SARS-CoV-2 protein (N-RBD$^{WT}$), which comprises spike receptor-binding domain (RBD) of SARS-CoV-2 lineage A fused with a domain of nucleocapsid protein, was generated for use as a nasal vaccine booster without adjuvant. A mouse vaccination model was designed to determine the booster efficacy (FIG. 1A). Briefly, groups of mice first completed the primary vaccination by intramuscular injection of two doses of COVID-19 mRNA vaccine (BioNTech) with a time interval of fourteen days between the two injections. Fourteen days after the second dose (of mRNA vaccine), the nasal vaccine booster (18 μg per mouse) or PBS (20 μL) were administered intranasally to the mice. Sera and bronchoalveolar lavage (BAL) fluids were collected for the detection of RBD-specific antibodies and nAbs against parental SARS-CoV-2 and variants.

Generation of Chimeric SARS-CoV-2 Protein (N-RBD)

Recombinant proteins were expressed using Expi293F expression system (Gibco). Gene sequences were codon-optimized and cloned into expression plasmids. For the N-RBD$^{WT}$ nasal booster, SARS-CoV-2 nucleocapsid protein (44-180aa of SEQ ID NO: 3) and "wild-type" spike RBD (306-541aa of SEQ ID NO: 1) derived from SARS-CoV-2 A lineage were fused together by PCR and cloned into expression construct with a N-terminal 6xHis tag. To express mammalian recombinant proteins, plasmids constructs were transfected into Expi293F cells using Expifectamine 293 transfection reagent (Gibco) following manufacturer's instruction and incubated for 72-96 hours. For protein purification, culture supernatant was harvested by centrifugation followed by filtration using 0.22 μm filters (Millipore) and passed through Ni Sepharose Excel resin (Cytiva). The resin was then washed, and proteins were eventually eluted with buffer containing 160 mM imidazole. Recombinant proteins were concentrated, and buffer exchanged using Pierce Protein Concentrator (Thermo).

Generation of Mouse Vaccination Model

Female 7-weeks old BALB/c mice were immunized intramuscularly with two doses (14 days in between) of COVID-19 mRNA vaccine (BioNTech) under anesthesia. Each dose comprised of 1 μg of mRNA vaccine per mouse. N-RBD protein boosters were dissolved in PBS/10% glycerol and administered intranasally (20 μL) to the mice left nostril under anesthesia at a dose of 18 μg protein per mouse. Control group was given PBS intranasally after two doses of intramuscular mRNA vaccine. Blood was collected from face vein at indicated timepoints and was centrifuged for serum collection. Animals were sacrificed by an overdose of anesthesia at the experiment endpoint. Bronchoalveolar lavage fluid was collected by inserting a catheter in the trachea of the terminally anesthetized mice, followed by instilling PBS into the bronchioles and lung. The collected fluid was centrifuged, and the supernatant was collected for downstream analysis.

Enzyme-Linked ImmunoSorbent Assay (ELISA)

Antibody titers were determined by in-house established enzyme-linked immunosorbent assay (ELISA). High-binding 96-well microplates (Corning 3690) were coated with 5 μg/mL recombinant SARS-CoV-2 spike RBD (306-541aa) protein, or with nucleocapsid protein in sodium carbonate buffer at 4° C. for overnight. The next day, microplates were washed, blocked, and serially diluted samples were added. Bound antibodies were detected by HRP-conjugated secondary antibodies to mouse IgG (Abcam) or mouse IgA (Invitrogen) and 1-Step Ultra TMB-ELISA Substrate Solution (Thermo). Absorbance at 450 nm was measured using Vatioskan LUX multimode microplate reader (Thermo) with Skanit Software version 6.1.0.51. Titers were calculated in GraphPad Prism 8 by performing 4-parameter logistical fitting on the absorbance data at each dilution. Antibody endpoint titers were determined as the interpolated reciprocal of the dilution giving the absorbance equivalent to the mean of control wells plus two standard deviations.

Cell Culture and Viruses

VeroE6 cells were cultured in DMEM (Gibco) supplemented with 10% fetal bovine serum (FBS) (Gibco). Viruses were isolated from clinical samples and cultured in BSL-3 laboratory. The accession number of representative SARS-CoV strains used in this study are MT230904 (WHO1), MW856793 (B.1.36/D614G), 0M212471 (B.1.617.2/Delta), and (B.1.1.529/Omicron). Detailed information of the viruses is as listed in the table below:

| | VOC | Pango lineage | host | GenBank | Accession ID |
|---|---|---|---|---|---|
| Parental (WH01) | N/A | A | human | MT230904 | EPI_ISL_434571 |
| D614G | N/A | B.1.36.27 | human | MW856793 | EPI_ISL_1472376 |
| Delta | Delta | B.1.617.2 | human | OM212471 | EPI_ISL_3221329 |
| Omicron | Omicron | B.1.1.529 | human | OM212472 | EPI_ISL_7138045 |

Authentic SARS-CoV-2 Virus Neutralization

Virus neutralization was quantitatively determined by in-house focus reduction neutralization assay and performed in BSL-3 laboratory. Briefly, VeroE6 cells were seeded in 96-well black plates (SPL) the day before the assay. On the day of assay, samples were serially diluted and incubated with 100-300 focus forming units (FFUs) of authentic live SARS-CoV-2 virus (A/WH01, B.1.36/D614G, B.1.617.2/Delta, B.1.1.529/Omicron) for 1 hour at 37° C. Sample-virus mixes were then transferred to VeroE6 cells for 1 hour at 37° C. for inoculation. Cells were washed with PBS and replenished with culture medium containing 1% FBS. Inoculated cells were further incubated for 6 hours. At the assay endpoint, cells were fixed with 4% formalin. Fixed cells were washed with PBS, permeabilized with 0.1% NP40, blocked with 2% BSA, and stained with in-house rabbit anti-SARS-CoV-2 nucleocapsid protein polyclonal antibody and detected by anti-rabbit Alexaflour 488 (Abcam). Fluorescent positive foci were detected by Cytation 7 Cell Imaging Multi-Mode Reader (Biotek) with GenS Image Prime version 3.11.19. Neutralization titers were calculated and determined in GraphPad Prism 8 by performing 4-parameter logistical fitting on the detected fluorescent loci at each dilution. The 50% focus reduction neutralization titer (FRNT50) was determined as the interpolated reciprocal of the dilution having 50% reduction of infected fluorescent loci compared to control wells.

Results

Figure 1B:
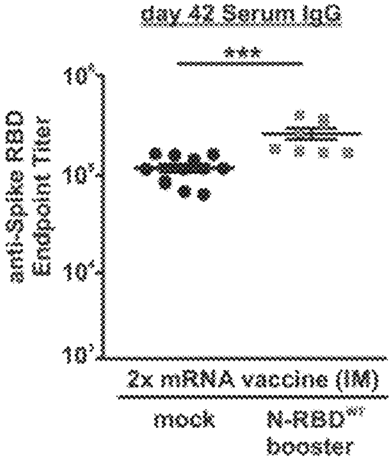
FIG. 1B shows the Serum anti-SARS-CoV-2 spike RBD antibody at day 42 for mice having received the N-RBD$^{WT}$ booster versus mice in control group (mock), as detected by ELISA and presented as IgG endpoint titer.
Figure 1C:
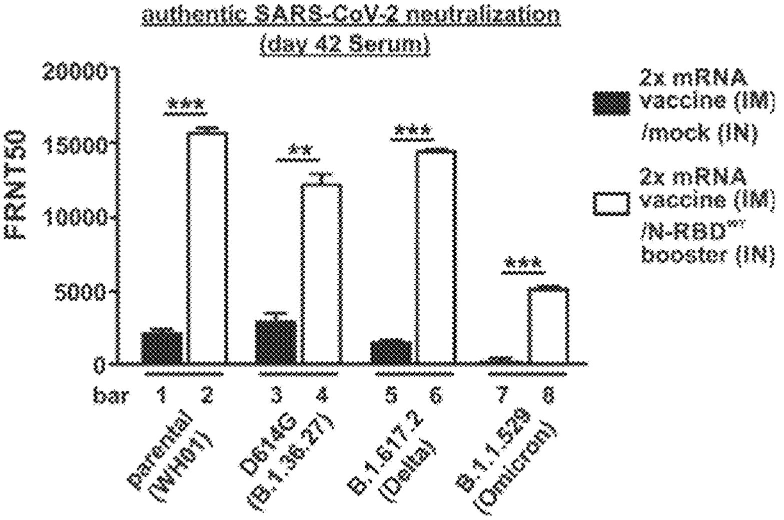
FIG. 1C shows the SARS-CoV-2 virus neutralization by pooled sera from day 42 for mice having received the N-RBD$^{WT}$ booster versus mice in control group (mock), as quantitated by focus reduction neutralization (FRNT) assay. Data were shown as the reciprocal of dilution where 50% focus reduction was detected (FRNT$_{50}$).

N-RBD$^{WT}$ Elicited RBD-Specific Antibodies and nAbs in Sera Against Parental SARS-CoV-2 and Variants Sera of mice vaccinated with two doses of COVID-19 mRNA vaccine contained high level of anti-RBD IgG antibodies, the mean endpoint titer of which reached $1.1\times10^5$. Surprisingly, the nasal booster could further boost the serum anti-RBD IgG level from $1.1\times10^5$ to $2.6\times10^5$ (FIG. 1B). Next, we examined the serum neutralizing ability against authentic live viruses including wild-type SARS-CoV-2 (Wuhan-Hu-1; WH01), D614G (B.1.36.27), delta (B.1.617.2) and omicron (B.1.1.529) variants (FIG. 1C). First, we showed that nasal booster greatly enhanced the authentic live virus neutralization against wild-type SARS-CoV-2 (Wuhan-Hu-1) from $FRNT_{50}=2.2\times10^3$ to $15.6\times10^3$ (bar 1 compared to bar 2, FIG. 1C). It is worthy to note that, without the nasal booster, there were a 30% and 86% reduction in neutralization against delta and omicron variants respectively (black bar 1 compared to black bar 5 and 7, FIG. 1C). In line with recent reports, neutralization against Omicron variant drastically dropped, which could account for the recent increasing number of breakthrough infections worldwide. Surprisingly, a single dose of nasal N-RBD$^{WT}$ booster not only potentiated the neutralization against authentic SARS-CoV-2 and delta variant, but also the omicron variant (hollow bar 6 and 8, FIG. 1C).

Figure 1D:
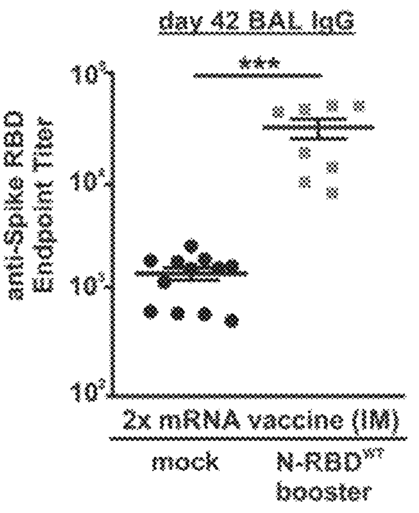
FIG. 1D shows the BAL anti-SARS-CoV-2 spike RBD IgG at day 42 for mice having received the N-RBD$^{WT}$ booster versus mice in control group (mock), as determined by ELISA.
Figure 1E:
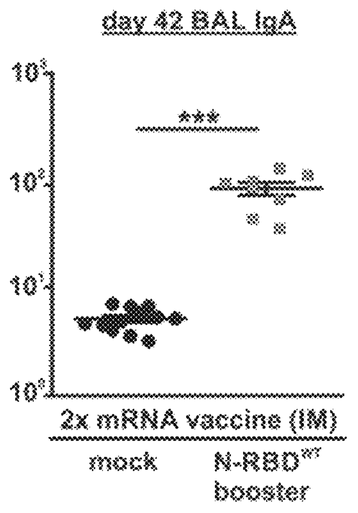
FIG. 1E shows the BAL anti-SARS-CoV-2 spike RBD IgA at day 42 for mice having received the N-RBD$^{WT}$ booster versus mice in control group (mock), as determined by ELISA.
Figure 1F:
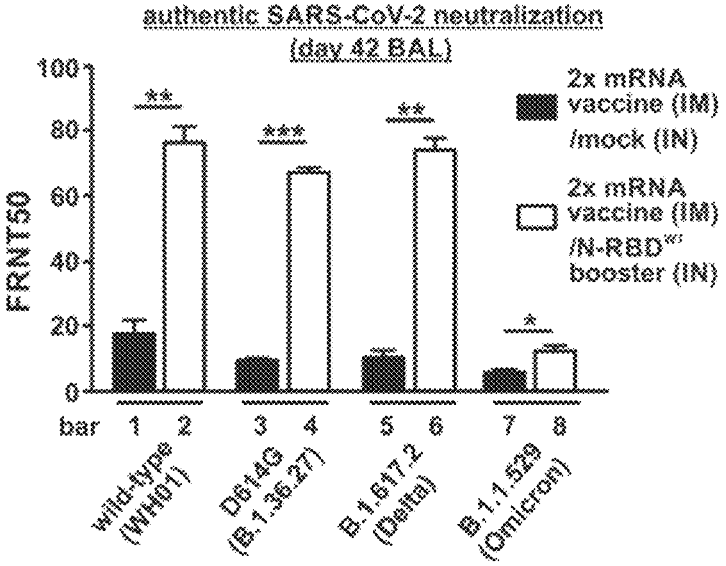
FIG. 1F shows SARS-CoV-2 virus neutralization by pooled BAL fluids from day 42 for mice having received the N-RBD$^{WT}$ booster versus mice in control group (mock), as quantitated by FRNT assay and presented as FRNT$_{50}$.

N-RBD$^{WT}$ Elicited RBD-Specific Antibodies and nAbs in BAL Against Parental SARS-CoV-2 and Variant Importantly, the N-RBD$^{WT}$ nasal booster strongly induced SARS-CoV-2-specific mucosal immunity as evidenced by the 21-fold increase in IgG and 11-fold increase in secreted IgA against RBD in BAL (FIGS. 1D and 1E). The booster also enhanced the degree of neutralization against wild-type, D614G, delta and omicron viruses in BAL fluids (FIG. 1F).

N-RBD$^{WT}$ Elicited N-Specific Antibodies

Figure 1G:
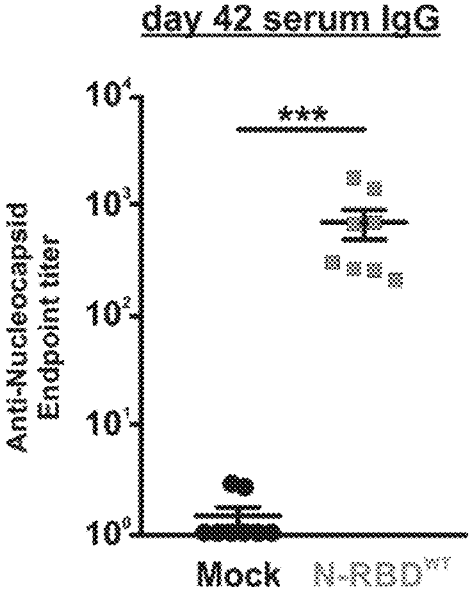
FIG. 1G shows the serum anti-SARS-CoV-2 nucleocapsid IgG at day 42 for mice having received the N-RBD$^{WT}$ booster versus mice in control group (mock), as determined by ELISA. Samples were measured in duplicates and all data points (8-12 replicates) were included in statistical analysis. Statistical tests were performed using two-tailed unpaired t-test. (*: p<0.1; :p<0.05; *:p<0.005; n.s.: not statistically significant).

As shown by FIG. 1G, a single dose of N-RBD$^{WT}$ could also elicit N-specific antibody, implying that the nasal booster not only enhanced the preimmunized anti-spike RBD antibody response, but also functioned as new immunogen.

Taken together, N-RBD$^{WT}$ was shown to boost the serum anti-RBD IgG level when used as a booster, as well as being capable of eliciting N-specific antibody, indicating that the chimeric SARS-CoV-2 protein could be used not only to enhance the preimmunized anti-spike RBD antibody response, but also functioned as new immunogen. N-RBD$^{WT}$ also greatly enhanced the serum neutralizing ability against authentic live viruses including wild-type SARS-CoV-2 strains and subsequent variants. Importantly, both the elevated endpoint titer of anti-spike RBD antibodies (antigen-specific IgA) in BAL and the enhanced neutralization against different variants of live SARS-CoV-2 viruses indicated successful induction of mucosal immunity.

Figure 2A:
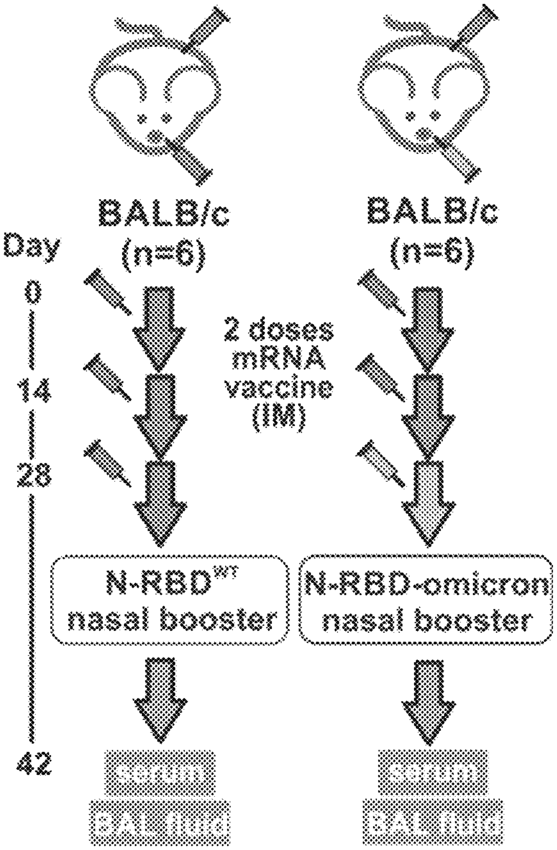
FIG. 2A shows the schematics of the experimental design for a nasal vaccine booster. All mice were intramuscularly injected with 2 doses of COVID-19 mRNA vaccine (1 μg per mouse), at 14 days apart. At day 28, 18 μg N-RBD$^{WT}$ or N-RBD$^{omicron}$ (recombinant omicron strain SARS-CoV-2 spike RBD fused with nucleocapsid NTD) was administered intranasally for the booster group (n=4 biological replicates). PBS was given intranasally for the control group (n=6 biological replicates). Sera and bronchoalveolar lavage (BAL) fluids were collected at day 42.

Example 2. Chimeric SARS-CoV-2 Protein (N-RBD$^{omicron}$) Comprising Omicron RBD as Booster Provided Strong Neutralizing Activity Against Omicron Variant without Compromising any Augmentation of Neutralization Against Wild-Type SARS-CoV-2 and Delta Variant Several reports clearly demonstrated that antibodies induced by the two-dose intramuscular injection of spike mRNA vaccine are less neutralizing against omicron variant. To illustrate the potential of chimeric SARS-CoV-2 protein to enhance neutralizing ability against new strains, the wild-type RBD of the N-RBD$^{WT}$ booster from Example 1 was replaced by the RBD from the omicron variant, and the mouse vaccination model from Example 1 was employed to study the neutralization activity against omicron variant as well as the neutralization against wild-type SARS-CoV-2 and delta variant. Briefly, groups of mice first completed the primary vaccination by intramuscular injection of two doses of COVID-19 mRNA vaccine (BioNTech) with a time interval of fourteen days between the two injections. Fourteen days after the second dose (of mRNA vaccine), the nasal vaccine booster (N-RBD$^{WT}$ or N-RBD$^{omicron}$) (18 μg per mouse) or PBS (20 μL) were administered intranasally to the mice (FIG. 2A). Sera and bronchoalveolar lavage (BAL) fluids were collected for the detection of RBD-specific antibodies and nAbs against parental SARS-CoV-2 and variants.

Specifically, the N-RBD$^{WT}$ chimeric protein was generated as described in Example 1. For the N-RBD$^{omicron}$ nasal booster, SARS-CoV-2 nucleocapsid protein (44-180aa of SEQ ID NO: 3) and omicron spike RBD (303-538aa of SEQ ID NO: 2) derived from SARS-CoV-2 B1.1.529 lineage were fused together by PCR and processed according to the method described in Example 1. The ELISA assays, cell and virus culture, as well as virus neutralization assays were carried out as described in Example 1.

Figure 2B:
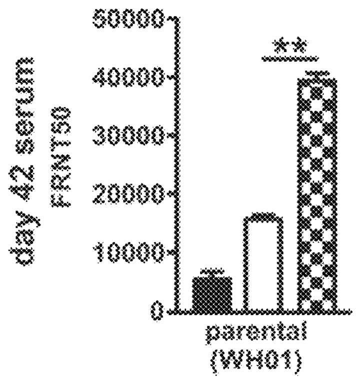
FIGS. 2B, C, D, E show the neutralization of parental (lineage A), D614G (lineage B1.36.27), Delta (B1.617.2) and Omicron (B.1.1.529) SARS-CoV-2 strains, respectively, by pooled sera obtained from N-RBD$^{WT}$ and N-RBD$^{omicron}$ booster groups at day 42 as quantitated by FRNT assay.
Figure 2C:
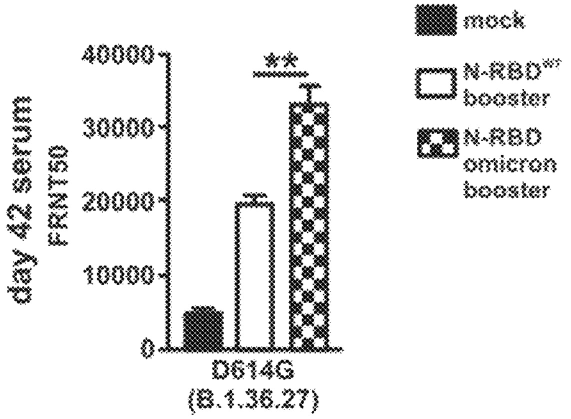
FIGS. 2F, G, H, I show the neutralization of parental (lineage A), D614G (lineage B1.36.27), Delta (B1.617.2) and Omicron (B.1.1.529) SARS-CoV-2 strains, respectively, by pooled BAL fluids obtained from N-RBD$^{WT}$ and N-RBD$^{omicron}$ booster groups at day 42 as quantitated by FRNT assay. Samples were measured in duplicates and all data points (8-12 replicates) were included in statistical analysis. Statistical tests were performed using two-tailed unpaired t-test. (*: p<0.1; :p<0.05; *:p<0.005; n.s.: not statistically significant).
Figure 2D:
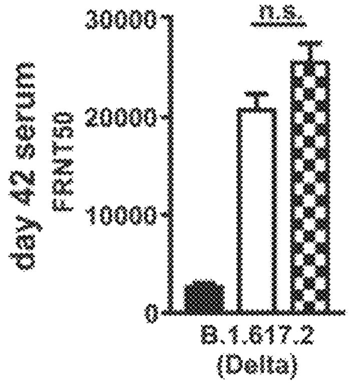
Figure 2E:
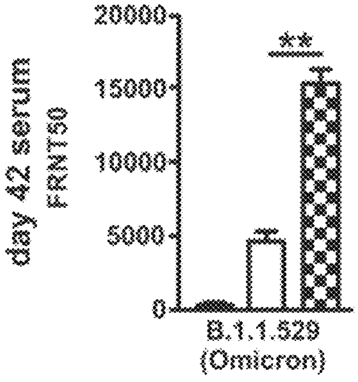
Figure 2F:
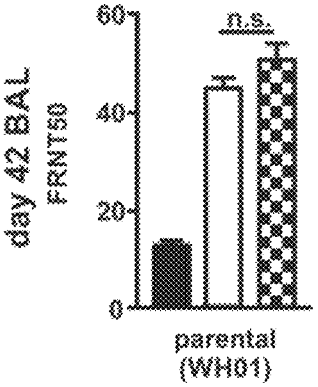
Figure 2G:
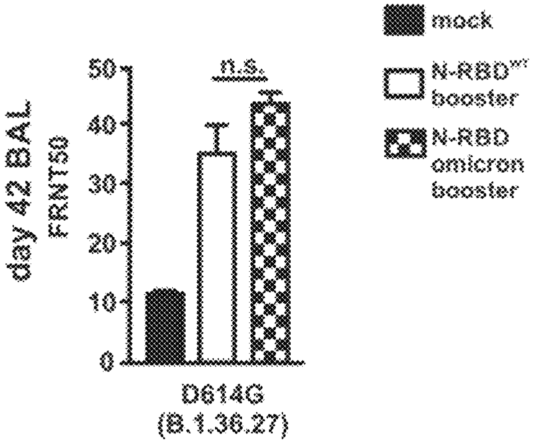
Figure 2H:
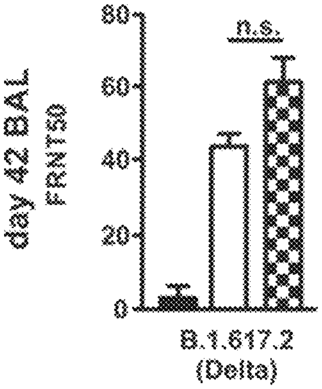
Figure 2I:
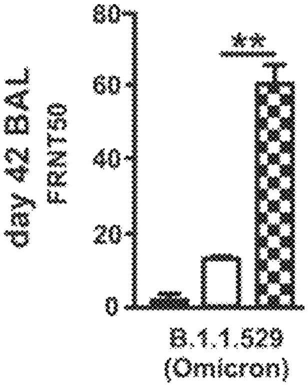

Serum and BAL fluid were obtained at 42 days post immunization and were both tested for authentic virus neutralization assay (illustrated in FIG. 2A). Serum antibodies elicited by two doses of mRNA vaccine could potently neutralize the parental SARS-CoV-2 infection only ($FRNT_{50}=6\times10^3$, black bar in FIG. 2B), but not the omicron infection ($FRNT_{50}=5\times10^2$, black bar in FIG. 2E). Both N-RBD$^{WT}$ and N-RBD$^{omicron}$ booster potently enhanced the serum neutralizing activity against wild-type, D614G, delta and omicron virus infection, respectively (hollow bars and checkered bars, respectively, in FIGS. 2B, 2C, 2D and 2E). The N-RBD$^{WT}$ and N-RBD$^{omicron}$ booster also enhanced the BAL neutralizing activity against wild-type, D614G, delta and omicron virus infection, respectively (hollow bars and checkered bars, respectively, in FIGS. 2F, 2G, 2H, 2I). Most importantly, N-RBD° micron potently enhanced the neutralizing activity (in sera as well as in BAL) against authentic omicron virus infection (checkered bars, in FIGS. 2E and 21). The effect elicited by a single dose of N-RBD$^{omicron}$ booster was unprecedently effective, reaching $FRNT_{50}=1.5\times10^4$ against the omicron variant (FIG. 2E).

Taken together, N-RBD$^{omicron}$ booster potently enhanced the neutralization activity against the omicron variant without compromising any augmentation of neutralization against the wild-type SARS-CoV-2 and delta variant, and the effect was observed both in sera and BAL (indicative of mucosal immunity). Since the omicron variant predominantly infects the upper respiratory tract and displays high transmissibility, further development of N-RBD$^{omicron}$ into human nasal vaccine booster could help control the spread of the circulating variants including the omicron variant.

The invention claimed is:

1. A chimeric protein comprising a receptor binding domain ("RBD") of a SARS-COV-2 spike protein ("S protein") fused to a booster enhancer domain ("BED"), wherein the BED comprises a fragment or a variant thereof of a nucleocapsid protein ("N protein") of a coronavirus, wherein the BED enhances the booster function of the RBD, and wherein the RBD comprises a fragment or a variant thereof of an S protein of the omicron variant of SARS-COV-2 (SARS-COV-2 lineage B.1.1.529).

2. The chimeric protein of claim 1, wherein the RBD is 200 to 300 amino acids long.

3. The chimeric protein of claim 1, wherein the N protein of the coronavirus is an N protein of a SARS-COV-2 virus.

4. The chimeric protein of claim 3, wherein the N protein of SARS-CoV-2 comprises the amino acid sequence of SEQ ID NO:3.

5. The chimeric protein of claim 4, wherein the BED comprises amino acids 44-180 of SEQ ID NO:3.

6. The chimeric protein of claim 1, wherein the BED is 100 to 150 amino acids long.

7. The chimeric protein of claim 1, wherein the BED is fused directly to the RBD.

8. The chimeric protein of claim 1, wherein the BED is fused to the RBD via a linker.

9. The chimeric protein of claim 1, wherein the BED is fused to the C-terminus of the RBD.

10. The chimeric protein of claim 1, wherein the BED is fused to the N-terminus of the RBD.

11. The chimeric protein of claim 4, wherein the fragment of the N protein comprises at least 100 amino acids of SEQ ID NO:3.

12. The chimeric protein of claim 11, wherein the variant of the fragment of the N protein differs from the fragment of the N protein by no more than 30 amino acid residues.

13. The chimeric protein of claim 1, wherein the fragment of the S protein comprises at least 200 amino acids of SEQ ID NO:2.

14. A chimeric protein comprising a receptor binding domain ("RBD") of a SARS-COV-2 spike protein ("S protein") fused to a booster enhancer domain ("BED"), wherein the BED comprises a fragment or a variant thereof of a nucleocapsid protein ("N protein") of a coronavirus, wherein the BED enhances the booster function of the RBD, and wherein the chimeric protein comprises the amino acid sequence of SEQ ID NO:4 or 5, or a variant thereof having at least 80% sequence homology to SEQ ID NO:4 or 5.

15. A vaccine booster composition comprising the chimeric protein of claim 1.

16. A nucleic acid or a vector encoding the chimeric protein of claim 1.

17. A method of enhancing the effect of a vaccine against SARS-COV-2 in an individual who has been vaccinated, comprising administering to the individual an effective amount of a vaccine booster composition, wherein the vaccine booster composition is administered intranasally, wherein the vaccine booster composition comprises a chimeric protein, wherein the chimeric protein comprises a receptor binding domain ("RBD") of a SARS-COV-2 spike protein ("S protein") fused to a booster enhancer domain ("BED"), wherein the BED comprises a fragment or a variant thereof of a nucleocapsid protein ("N protein") of a coronavirus, and wherein the BED enhances the booster function of the RBD.

18. The method of claim 17, wherein the vaccine booster composition is administered at least 7 days after the administration of the vaccine.

19. The method of claim 18, wherein the vaccine booster composition is administered about 4 to about 6 weeks after the administration of the vaccine.

20. The method of claim 17, wherein the individual has been administered with at least two doses of the vaccine prior to the administration of the vaccine booster composition.

21. A method of producing a chimeric protein, comprising expressing the nucleic acid or the vector of claim 16 in a host cell, thereby obtaining the chimeric protein.

22. The method of claim 17, wherein the BED is fused to the N-terminus of the RBD.

23. The method of claim 17, wherein the N protein of the coronavirus is an N protein of a SARS-COV-2 virus.

24. The method of claim 17, wherein the RBD comprises a fragment or a variant thereof of an S protein of the omicron variant of SARS-COV-2 (SARS-COV-2 lineage B.1.1.529).

25. The method of claim 17, wherein the RBD comprises a fragment or a variant thereof of an S protein of SARS-COV-2 lineage A.

* * * * *

SEQUENCE LISTING

```
Sequence total quantity: 5
SEQ ID NO: 1           moltype = AA  length = 1273
FEATURE                Location/Qualifiers
source                 1..1273
                       mol_type = protein
                       organism = Severe acute respiratory syndrome coronavirus 2
SEQUENCE: 1
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
```

-continued

```
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                   1273

SEQ ID NO: 2            moltype = AA  length = 1270
FEATURE                 Location/Qualifiers
source                  1..1270
                        mol_type = protein
                        organism = Severe acute respiratory syndrome coronavirus 2
SEQUENCE: 2
MFVFLVLLPL VSSQCVNLTT RTQLPPAYTN SFTRGVYYPD KVFRSSVLHS TQDLFLPFFS  60
NVTWFHVISG TNGTKRFDNP VLPFNDGVYF ASIEKSNIIR GWIFGTTLDS KTQSLLIVNN  120
ATNVVIKVCE FQFCNDPFLD HKNNKSWMES EFRVYSSANN CTFEYVSQPF LMDLEGKQGN  180
FKNLREFVFK NIDGYFKIYS KHTPIIVREP EDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNLAP FFTFKCYGVS PTKLNDLCFT NVYADSFVIR GDEVRQIAPG QTGNIADYNY  420
KLPDDFTGCV IAWNSNKLDS KVSGNYNYLY RLFRKSNLKP FERDISTEIY QAGNKPCNGV  480
AGFNCYFPLR SYSFRPTYGV GHQPYRVVVL SFELLHAPAT VCGPKKSTNL VKNKCVNFNF  540
NGLKGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHRR ARSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFKGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDIFSR LDKVEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                       1270

SEQ ID NO: 3            moltype = AA  length = 419
FEATURE                 Location/Qualifiers
source                  1..419
                        mol_type = protein
                        organism = Severe acute respiratory syndrome coronavirus 2
SEQUENCE: 3
MSDNGPQNQR NAPRITFGGP SDSTGSNQNG ERSGARSKQR RPQGLPNNTA SWFTALTQHG  60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAFFGMSRI GMEVTPSGTW LTYTGAIKLD DKDPNFKDQV ILLNKHIDAY  360
KTFPPTEPKK DKKKKADETQ ALPQRQKKQQ TVTLLPAADL DDFSKQLQQS MSSADSTQA   419

SEQ ID NO: 4            moltype = AA  length = 417
FEATURE                 Location/Qualifiers
source                  1..417
                        mol_type = protein
                        organism = Severe acute respiratory syndrome coronavirus 2
SEQUENCE: 4
MDAMKRGLCC VLLLCGAVFV SPSAAHHHHH HGGGGSLEVL FQGPGLPNNT ASWFTALTQH  60
GKEDLKFPRG QGVPINTNSS PDDQIGYYRR ATRRIRGGDG KMKDLSPRWY FYYLGTGPEA  120
GLPYGANKDG IIWVATEGAL NTPKDHIGTR NPANNAAIVL QLPQGTTLPK GFYAEGSRGG  180
SFTVEKGIYQ TSNFRVQPTE SIVRFPNITN LCPFGEVFNA TRFASVYAWN RKRISNCVAD  240
YSVLYNSASF STFKCYGVSP TKLNDLCFTN VYADSFVIRG DEVRQIAPGQ TGKIADYNYK  300
LPDDFTGCVI AWNSNNLDSK VGGNYNYLYR LFRKSNLKPF ERDISTEIYQ AGSTPCNGVE  360
GFNCYFPLQS YGFQPTNGVG YQPYRVVVLS FELLHAPATV CGPKKSTNLV KNKCVNF     417

SEQ ID NO: 5            moltype = AA  length = 417
FEATURE                 Location/Qualifiers
source                  1..417
                        mol_type = protein
                        organism = Severe acute respiratory syndrome coronavirus 2
SEQUENCE: 5
MDAMKRGLCC VLLLCGAVFV SPSAAHHHHH HGGGGSLEVL FQGPGLPNNT ASWFTALTQH  60
GKEDLKFPRG QGVPINTNSS PDDQIGYYRR ATRRIRGGDG KMKDLSPRWY FYYLGTGPEA  120
GLPYGANKDG IIWVATEGAL NTPKDHIGTR NPANNAAIVL QLPQGTTLPK GFYAEGSRGG  180
SFTVEKGIYQ TSNFRVQPTE SIVRFPNITN LCPFDEVFNA TRFASVYAWN RKRISNCVAD  240
YSVLYNLAPF FTFKCYGVSP TKLNDLCFTN VYADSFVIRG DEVRQIAPGQ TGNIADYNYK  300
LPDDFTGCVI AWNSNKLDSK VSGNYNYLYR LFRKSNLKPF ERDISTEIYQ AGNKPCNGVA  360
GFNCYFPLRS YSFRPTYGVG HQPYRVVVLS FELLHAPATV CGPKKSTNLV KNKCVNF     417
```